(12) United States Patent
Czekaj et al.

(10) Patent No.: US 7,361,663 B2
(45) Date of Patent: Apr. 22, 2008

(54) N-ACYLPYRROLIDIN-2-YLALKYLBENZAMI-DINE DERIVATIVES AS INHIBITORS OF FACTOR XA

(75) Inventors: Mark Czekaj, Doylestown, PA (US); Scott I. Klein, Collegeville, PA (US); Heinz W. Pauls, Oakville (CA)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 468 days.

(21) Appl. No.: 10/686,871

(22) Filed: Oct. 16, 2003

(65) Prior Publication Data

US 2004/0087570 A1 May 6, 2004

Related U.S. Application Data

(63) Continuation-in-part of application No. 10/143,190, filed on May 10, 2002, now abandoned, which is a continuation of application No. PCT/EP00/10890, filed on Nov. 4, 2000.

(60) Provisional application No. 60/164,621, filed on Nov. 10, 1999.

(30) Foreign Application Priority Data

Dec. 23, 1999 (GB) .................................. 9930540.1

(51) Int. Cl.
| | |
|---|---|
| A61P 9/00 | (2006.01) |
| A61K 31/517 | (2006.01) |
| A61K 31/44 | (2006.01) |
| A61K 31/47 | (2006.01) |
| A61K 31/415 | (2006.01) |
| A61K 31/40 | (2006.01) |
| C07D 239/00 | (2006.01) |
| C07D 401/00 | (2006.01) |
| C07D 217/00 | (2006.01) |
| C07D 403/00 | (2006.01) |
| C07D 207/00 | (2006.01) |
| C07D 405/00 | (2006.01) |

(52) U.S. Cl. .................... 514/266.2; 514/300; 514/310; 514/385; 514/422; 514/423; 514/343; 544/283; 544/293; 546/113; 546/143; 546/278.4; 546/279.1; 548/314.7; 548/525; 548/539; 548/540

(58) Field of Classification Search ............. 514/266.2, 514/300, 310, 385, 422, 423, 343; 544/283, 544/293; 546/113, 143, 279.1, 278.4; 548/314.7, 548/525, 539, 540
See application file for complete search history.

(56) References Cited

U.S. PATENT DOCUMENTS 6,147,100 A 11/2000 Seno et al. .................. 514/369

FOREIGN PATENT DOCUMENTS

| JP | 11246554 A2 * | 9/1999 |
|---|---|---|
| WO | WO 97/45424 A1 * | 12/1997 |
| WO | WO 98 01428 | 1/1998 |
| WO | WO 9833797 A1 * | 8/1998 |
| WO | WO 00 37458 | 6/2000 |

OTHER PUBLICATIONS

West, Anthony R., Solid State Chemistry and its Applications, Wiley, New York, 1988, pp. 358 & 365.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Arisawa, Mitsuhiro; Takezawa, Emiko; Nishida, Atsushi; Mori, Miwako; Nakagawa, Masako, Synlett (10), 1179-1180 (English) 1997.*
Neukomm, G.; Roessler, F.; Johne, S.; Hesse, M., Planta Medica, 48(4), 246-52 (German) 1983.*
Arisawa, Mitsuhiro et al., Construction of Chiral 1,2-Cycloalkanopyrrolidines from L-Proline Using Ring Closing Metathesis (RCM), Chem. Pharm. Bull (2000), 48(10), 1593-1596.
Han, William T. et al., Azetidin-2-One Derivatives as Inhibitors of Thrombin, Bioorganic & Medicinal Chemistry, Elsevier Scient Ltd, GB, vol. 3, No. 8, 1995, pp. 1123-1143.
Herbert, Richard B. et al., Synthesis of (.+ . .)-Norruspoline, J. Chem. Res. Synop. (1982), (11), p. 299.
Okada, Midori et al., Fluoro-Lactonization of 4-Alkenoic Acid Derivatives with N-Fluoropentachloropyridinium Triflate, J. Flourine Chem. (1997), 82(2), 157-161.
Roessler, Felix et al., Ruspolia Hypercrateriformis M.R.: Isolation and Structure Elucidation of New Pyrrolidine Alkaloids, Helv. Chim. Acta (1978), vol. 61, Fasc. 3, 1200-1206.
Shan, Daxian, et al., Prodrug Strategies Based on Intromolecular Cyclization Reactions, J. Pharmaceutical Sciences, 1997, 86, pp. 765-767.

* cited by examiner

Primary Examiner—Brenda L Coleman
(74) Attorney, Agent, or Firm—Jiang Lin; Raymond S. Parker, III

(57) ABSTRACT

This invention is directed to N-acylpyrrolidin-2-ylalkylbenzamidine derivatives which useful for inhibiting the activity of Factor Xa, by contacting said derivatives with a composition containing Factor Xa. The present invention is also directed to compositions containing said derivatives, methods for their preparation, their use, such as in inhibiting the formation of thrombin or for treating a patient suffering from, or subject to, a disease state associated with a physiologically detrimental excess amount of thrombin.

20 Claims, No Drawings

N-ACYLPYRROLIDIN-2-YLALKYLBENZAMIDINE DERIVATIVES AS INHIBITORS OF FACTOR XA

CROSS REFERENCE

This application is a continuation-in-part of pending U.S. patent application Ser. No. 10/143,190, filed May 10, 2002, which is a continuation of International application No. PCT/EP00/10890, filed Nov. 4, 2000, which claims the benefit of U.S. Provisional Application No. 60/164,621, filed Nov. 10, 1999.

FIELD OF THE INVENTION

The compounds of formula I are useful for inhibiting the activity of Factor Xa, and also, exhibit useful pharmacological activity. Accordingly the compounds are incorporated into pharmaceutical compositions and used in the treatment of patients suffering from certain medical disorders. More especially, they are Factor Xa inhibitors. The present invention is directed to compounds of formula I, intermediates thereof, compositions containing compounds of formula I, and their use, inclusive of inhibiting Factor Xa and treating a patient suffering from, or subject to, physiological conditions ameliorable by administering to said patient a pharmaceutically acceptable amount of said inhibitor of Factor Xa.

Factor Xa is the penultimate enzyme in the coagulation cascade. Both free Factor Xa and Factor Xa assembled in the prothrombinase complex (Factor Xa, Factor Va, calcium and phospholipid) are inhibited by compounds of formula I. Factor Xa inhibition is obtained by direct complex formation between the inhibitor and the enzyme and is therefore independent of the plasma co-factor antithrombin III. Effective Factor Xa inhibition is achieved by administering the compounds either by oral administration, continuous intravenous infusion, bolus intravenous administration or any other parenteral route such that it achieves the desired effect of preventing the Factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening clots throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

SUMMARY OF THE INVENTION

This invention is directed to a compound of formula I which is useful for inhibiting the activity of Factor Xa, by contacting said compound with a composition containing Factor Xa, where said compound is as follows:

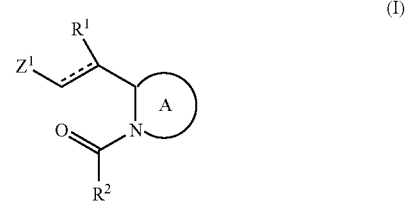

wherein

----- is a single or double bond $R^1$ is hydrogen, $-CO_2R^3$, $-C(O)R^3$, $-CONR^3R^3$, $-CH_2OR^4$ or $-CH_2SR^4$;

ring A is an optionally substituted 4 to 7 membered azaheterocyclyl ring or an optionally substituted 4 to 7 membered azaheterocyclenyl ring;

$R^2$ is alkyl, alkenyl, alkynyl, optionally substituted cycloalkyl, optionally substituted cycloalkenyl, optionally substituted heterocyclyl, optionally substituted heterocyclenyl, optionally substituted aryl, optionally substituted heteroaryl, optionally substituted aralkyl, optionally substituted heteroaralkyl, optionally substituted aralkenyl, optionally substituted heteroaralkenyl, optionally substituted aralkynyl, or optionally substituted heteroaralkynyl;

$R^3$ is hydrogen or lower alkyl;

$R^4$ is hydrogen, lower alkyl, $Z^2$-(lower alkyl), lower acyl, aroyl or heteroaroyl; and $Z^1$ is substituted aryl, substituted cycloalkyl, substituted cycloalkenyl, optionally substituted heteroaryl, optionally substituted heterocyclyl, optionally substituted heterocyclenyl, substituted fused arylcycloalkyl, substituted fused arylcycloalkenyl, optionally substituted fused heteroarylcycloalkyl, optionally substituted fused heteroarylcycloalkenyl, optionally substituted fused heteroarylheterocyclyl, optionally substituted fused heteroarylheterocyclenyl; or a pharmaceutically acceptable salt thereof, an N-oxide thereof, a solvate thereof, an acid bioisostere thereof, or prodrug thereof, provided that when $Z^1$ is substituted solely by amidino or N—($R^9O_2C$—, $R^9O$—, HO—, $R^9C(O)$—, HCO— or lower alkyl) substituted amidino; wherein $R^9$ is alkyl, then $Z^1$ is other than indoyl, benzofuranyl, benzothienyl, benzoimidazolyl, benzoxazolyl, benzothiazolyl, naphthyl, tetrahydronaphthyl, indanyl, dihydrobenzofuranyl and dihydrobenzothienyl; or substituted aryl, substituted cycloalkyl, or substituted cycloalkenyl, then it is substituted by, at least, a moiety of the formula

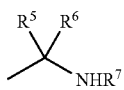

wherein $R^7$ is hydrogen, and $R^5$ and $R^6$ are hydrogen or together are $=NR^8$, and $R^8$ is selected from hydrogen, $R^9O_2C-$, $R^9O-$, $HO-$, $R^9C(O)-$, $HCO-$, cyano, optionally substituted lower alkyl, nitro or $Y^{1a}Y^{2a}N-$; wherein $R^9$ is alkyl, optionally substituted aralkyl, or optionally substituted heteroaralkyl, and $Y^{1a}$ and $Y^{2a}$ are independently hydrogen or alkyl.

The present invention is also directed to compositions containing compounds of the formula I, methods for their preparation, their use, such as in inhibiting the formation of thrombin or for treating a patient suffering from, or subject to, a disease state associated with a physiologically detrimental excess amount of thrombin.

DETAILED DESCRIPTION OF THE INVENTION

As used above, and throughout the description of the invention, the following terms, unless otherwise indicated, shall be understood to have the following meanings:

Definitions

"Acid bioisostere" means a group which has chemical and physical similarities producing broadly similar biological properties to a carboxy group (see Lipinski, Annual Reports in Medicinal Chemistry, 1986, 21, p.283 "Bioisosterism In Drug Design"; Yun, Hwahak Sekye, 1993, 33, p.576-579 "Application Of Bioisosterism To New Drug Design"; Zhao, Huaxue Tongbao, 1995, p.34-38 "Bioisosteric Replacement And Development Of Lead Compounds In Drug Design"; Graham, Theochem, 1995, 343, p.105-109 "Theoretical Studies Applied To Drug Design:ab initio Electronic Distributions In Bioisosteres"). Examples of suitable acid bioisosteres include: $-C(=O)-NHOH$, $-C(=O)-CH_2OH$, $-C(=O)-CH_2SH$, $-C(=O)-NH-CN$, sulpho, phosphono, alkylsulphonylcarbamoyl, tetrazolyl, arylsulphonylcarbamoyl, heteroaryl-sulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group may be substituted by one or more halo or cycloalkyl group. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkoxy" means an alkyl-O— group wherein the alkyl group is as herein described. Exemplary alkoxy groups include methoxy, ethoxy, n-propoxy, i-propoxy, n-butoxy and heptoxy.

"Alkoxyalkyl" means an alkyl-O-alkyl-group wherein the alkyl groups are independent as herein described. Exemplary alkoxy groups include methoxyethyl, ethoxymethyl, n-butoxymethyl and cyclopentylmethyloxyethyl.

"Alkoxycarbonyl" means an alkyl-O—CO— group, wherein the alkyl group is as herein defined. Exemplary alkoxycarbonyl groups include methoxycarbonyl, ethoxycarbonyl, or t-butyloxycarbonyl.

"Alkyl" means an aliphatic hydrocarbon group which may be straight or branched having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl may be substituted with one or more "alkyl group substituents" which may be the same or different, and include halo, cycloalkyl, carboxy, alkoxycarbonyl, aralkyloxycarbonyl, heteroaralkyloxycarbonyl or $Y^1Y^2NCO-$, wherein $Y^1$ and $Y^2$ are independently hydrogen, optionally substituted alkyl, optionally substituted aryl, optionally substituted aralkyl or optionally substituted heteroaralkyl, or $Y^1$ and $Y^2$ taken together with the N through which $Y^1$ and $Y^2$ are linked form a 4 to 7 membered heterocyclyl. Exemplary alkyl groups include methyl, trifluoromethyl, cyclopropylmethyl, cyclopentylmethyl, ethyl, n-propyl, i-propyl, n-butyl, t-butyl, n-pentyl, 3-pentyl, carboxymethyl, methoxycarbonylethyl, benzyloxycarbonylmethyl, pyridylmethyloxycarbonylmethyl.

"Alkylsulfinyl" means an alkyl-SO— group wherein the alkyl group is as defined above. Preferred groups are those wherein the alkyl group is lower alkyl.

"Alkylsulfonyl" means an alkyl-$SO_2$-group wherein the alkyl group is as defined above. Preferred groups are those wherein the alkyl group is lower alkyl.

"Alkylthio" means an alkyl-S— group wherein the alkyl group is as herein described. Exemplary alkylthio groups include methylthio, ethylthio, i-propylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Branched means that one or more lower alkyl groups such as methyl, ethyl or propyl are attached to a linear alkynyl chain. "Lower alkynyl" means about 2 to about 4 carbon atoms in the chain which may be straight or branched. The alkynyl group may be substituted by one or more halo. Exemplary alkynyl groups include ethynyl, propynyl, n-butynyl, 2-butynyl, 3-methylbutynyl, n-pentynyl, heptynyl, octynyl and decynyl.

"Amidino" or "amidine" means a group of formula

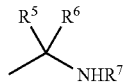

wherein $R^5$ and $R^6$ together are =$NR^8$ wherein $R^8$ is selected from hydrogen, $R^9O_2C$—, $R^9O$—, HO—, $R^9C(O)$—, HCO—, cyano, optionally substituted lower alkyl, nitro or $Y^{1a}Y^{2a}N$—; wherein $R^9$ is alkyl, optionally substituted aralkyl, or optionally substituted heteroaralkyl; $R^7$ is selected from hydrogen, optionally substituted lower alkyl, optionally substituted aralkyl and optionally substituted heteroaralkyl; and $Y^{1a}$ and $Y^{2a}$ are independently hydrogen or alkyl. Preferred amidino groups are those in which $R^5$ and $R^6$ are =$NR^8$, wherein $R^8$ is selected from hydrogen, $R^9O$, or optionally substituted lower alkyl and $R^7$ is as defined above. More preferred amidino groups are those in which $R^5$ and $R^6$ are =$NR^8$, and $R^7$ and $R^8$ are hydrogen.

"Amino acid" means an amino acid selected from the group consisting of natural and unnatural amino acids as defined herein. Preferred amino acids are those possessing an α-amino group. The amino acids may be neutral, positive or negative depending on the substituents in the side chain. "Neutral amino acid" means an amino acid containing uncharged side chain substituents. Exemplary neutral amino acids include alanine, valine, leucine, isoleucine, proline, phenylalanine, tryptophan, methionine, glycine, serine, threonine and cysteine. "Positive amino acid" means an amino acid in which the side chain substituents are positively charged at physiological pH. Exemplary positive amino acids include lysine, arginine and histidine. "Negative amino acid" means an amino acid in which the side chain substituents bear a net negative charge at physiological pH. Exemplary negative amino acids include aspartic acid and glutamic acid. Preferred amino acids are a-amino acids. The more preferred amino acids are α-amino acids having L-stereochemistry at the α-carbon. Exemplary natural amino acids are isoleucine, proline, phenylalanine, tryptophan, methionine, glycine, serine, threonine, cysteine, tyrosine, asparagine, glutamine, lysine, arginine, histidine, aspartic acid and glutamic acid.

"Amine protecting group" means an easily removable group which is known in the art to protect an amino group against undesirable reaction during synthetic procedures and to be selectively removable. The use of amine protecting groups is well known in the art for protecting groups against undesirable reactions during a synthetic procedure and many such protecting groups are known, cf, for example, T. H. Greene and P. G. M. Wuts, Protective Groups in Organic Synthesis, 2nd edition, John Wiley & Sons, New York (1991), incorporated herein by reference. Preferred amine protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-trimethylsilylethxoycarbonyl, vinyloxycarbonyl, allyloxycarbonyl, t-butyloxycarbonyl (BOC), 1,1-dimethylpropynyloxycarbonyl, benzyloxycarbonyl (CBZ), p-nitrobenzyloxycarbony, 2,4-dichlorobenzyloxycarbonyl, and the like.

"Acid labile amine protecting group" means an amine protecting group as defined above which is readily removed by treatment with acid while remaining relatively stable to other reagents. A preferred acid labile amine protecting group is tert-butoxycarbonyl (BOC).

"Hydrogenation labile amine protecting group" means an amine protecting group as defined above which is readily removed by hydrogenation while remaining relatively stable to other reagents. A preferred hydrogenation labile amine protecting group is benzyloxycarbonyl (CBZ).

"Hydrogenation labile acid protecting group" means an acid protecting group as defined above which is readily removed by hydrogenation while remaining relatively stable to other reagents. A preferred hydrogenation labile acid protecting group is benzyl.

"Aralkoxycarbonyl" means an aralkyl-O—CO— group wherein the aralkyl groups is as herein described. An exemplary aralkoxycarbonyl group is benzyloxycarbonyl.

"Aralkyl" means an aryl-alkyl-group wherein the aryl and alkyl are as herein described. Preferred aralkyls contain a lower alkyl moiety. Exemplary aralkyl groups include benzyl, 2-phenethyl and naphthlenemethyl.

"Aralkylamino" means an aryl-alkyl-NH— group wherein aryl and alkyl are as defined herein.

"Aralkylthio" means an aralkyl-S— group wherein the aralkyl group is as herein described. An exemplary aralkylthio group is benzylthio.

"Aromatic" means aryl or heteroaryl as defined below. Preferred aromatic groups include phenyl, halo substituted phenyl and azaheteroaryl.

"Aroyl" means an aryl-CO— group wherein the aryl group is as herein described. Exemplary groups include benzoyl and 1- and 2-naphthoyl.

"Aroylamino" is an aroyl-NH— group wherein aroyl is as defined herein.

"Aryl" means an aromatic monocyclic or multicyclic ring system of about 6 to about 14 carbon atoms, preferably of about 6 to about 10 carbon atoms. The aryl is optionally substituted with one or more "ring system substituents" which may be the same or different, and are as defined herein. Representative aryl groups include phenyl or naphthyl, or phenyl substituted or naphthyl substituted.

"Aryldiazo" means an aryl-azo-group wherein the aryl and azo groups are as defined herein.

"Fused arylcycloalkenyl" means a fused aryl and cycloalkenyl as defined herein. Preferred fused arylcycloalkenyls are those wherein the aryl thereof is phenyl and the cycloalkenyl consists of about 5 to about 6 ring atoms. A fused arylcycloalkenyl as a variable may be bonded through any atom of the ring system thereof capable of such. The fused arylcycloalkenyl may be optionally substituted by one or more ring system substituent, wherein the "ring system substituent" is as defined herein. Representative fused arylcycloalkenyl include 1,2-dihydronaphthylene, indene, and the like.

"Fused arylcycloalkyl" means a fused aryl and cycloalkyl as defined herein. Preferred fused arylcycloalkyls are those wherein the aryl thereof is phenyl and the cycloalkyl consists of about 5 to about 6 ring atoms. A fused arylcycloalkyl as a variable may be bonded through any atom of the ring system thereof capable of such. The fused arylcycloalkyl may be optionally substituted by one or more ring system substituent, wherein the "ring system substituent" is as defined herein. Representative fused arylcycloalkyl includes 1,2,3,4-tetrahydronaphthylene, and the like.

"Fused arylheterocyclenyl" means a fused aryl and heterocyclenyl as defined herein. Preferred fused arylheterocyclenyls are those wherein the aryl thereof is phenyl and the heterocyclenyl consists of about 5 to about 6 ring atoms. A fused arylheterocyclenyl as a variable may be bonded through any atom of the ring system thereof capable of such. The designation of the aza, oxa or thia as a prefix before heterocyclenyl portion of the fused arylheterocyclenyl define that at least a nitrogen, oxygen or sulfur atom is present respectively as a ring atom. The fused arylheterocyclenyl may be optionally substituted by one or more ring system substituent, wherein the "ring system substituent" is as defined herein. The nitrogen atom of a fused arylheterocyclenyl may be a basic nitrogen atom. The nitrogen or sulphur atom of the heterocyclenyl portion of the fused arylheterocyclenyl may also be optionally oxidized to the corresponding N-oxide, S-oxide or S,S-dioxide. Representative fused arylheterocyclenyl include 3H-indolinyl, 1H-2-oxoquinolyl, 2H-1-oxoisoquinolyl, 1,2-dihydroquinolinyl, 3,4-dihydroquinolinyl, 1,2-dihydroisoquinolinyl, 3,4-dihydroisoquinolinyl, and the like.

"Fused arylheterocyclyl" means a fused aryl and heterocyclyl as defined herein. Preferred fused arylheterocyclyls are those wherein the aryl thereof is phenyl and the heterocyclyl consists of about 5 to about 6 ring atoms. A fused arylheterocyclyl as a variable may be bonded through any atom of the ring system thereof capable of such. The designation of the aza, oxa or thia as a prefix before heterocyclyl portion of the fused arylheterocyclyl define that at least a nitrogen, oxygen or sulfur atom is present respectively as a ring atom. The fused arylheterocyclyl may be optionally substituted by one or more ring system substituent, wherein the "ring system substituent" is as defined herein. The nitrogen atom of a fused arylheteroaryl may be a basic nitrogen atom. The nitrogen or sulphur atom of the heterocyclyl portion of the fused arylheterocyclyl may also be optionally oxidized to the corresponding N-oxide, S-oxide or S,S-dioxide. Representative preferred fused arylheterocyl ring systems include indolinyl, 1,2,3,4-tetrahydroisoquinoline, 1,2,3,4-tetrahydroquinoline, 1H-2,3-dihydroisoindol-2-yl, 2,3-dihydrobenz[f]isoindol-2-yl, 1,2,3,4-tetrahydrobenz[g]isoquinolin-2-yl, and the like.

"Aryloxy" means an aryl-O— group wherein the aryl group is as defined herein. Exemplary groups include phenoxy and 2-naphthyloxy.

"Aryloxycarbonyl" means an aryl-O—CO— group wherein the aryl group is as defined herein. Exemplary aryloxycarbonyl groups include phenoxycarbonyl and naphthoxycarbonyl.

"Arylsulfonyl" means an aryl-SO2— group wherein the aryl group is as defined herein.

"Arylsulfinyl" means an aryl-SO— group wherein the aryl group is as defined herein.

"Arylthio" means an aryl-S— group wherein the aryl group is as herein described. Exemplary arylthio groups include phenylthio and naphthylthio.

"Basic nitrogen atom" means an $Sp^2$ or $Sp^3$ hybridized nitrogen atom having a non-bonded pair of electrons which is capable of being protonated. Examples of basic nitrogen atoms include optionally substituted imino, optionally substituted amino and optionally substituted amidino groups.

"Carboxy" means a HO(O)C— (carboxylic acid) group.

"Compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

"Cycloalkyl" means a non-aromatic mono- or multicyclic ring system of about 3 to about 10 carbon atoms, preferably of about 5 to about 10 carbon atoms. Preferred ring sizes of rings of the ring system include about 5 to about 6 ring atoms. The cycloalkyl is optionally substituted with one or more "ring system substituents" which may be the same or different, and are as defined herein. Representative monocyclic cycloalkyl include cyclopentyl, cyclohexyl, cycloheptyl, and the like. Representative multicyclic cycloalkyl include 1-decalin, norbornyl, adamant-(1- or 2-)yl, and the like. Preferred ring system substituents for a cycloalkyl are amidino or $Y^1Y^2N$— as defined herein.

"Cycloalkenyl" means a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. The cycloalkenyl is optionally substituted with one or more "ring system substituents" which may be the same or different, and are as defined herein. Representative monocyclic cycloalkenyl include cyclopentenyl, cyclohexenyl, cycloheptenyl, and the like. A representative multicyclic cycloalkenyl is norbornylenyl. Preferred ring system substituents for a cycloalkyl are amidino or $Y^1Y^2N$— as defined herein "Derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

"Di-alkylamino" means an (alkyl)(alkyl)-amino group wherein the alkyl groups are independent as herein defined.

"Diazo" means a bivalent —N=N— radical.

"Effective amount" is means an amount of a compound/composition according to the present invention effective in producing the desired therapeutic effect.

"Halo" means fluoro, chloro, bromo, or iodo. Preferred are fluoro, chloro or bromo, and more preferred are fluoro or chloro.

"Heteroaralkenyl" means an heteroaryl-alkenyl-group wherein the heteroaryl and alkenyl are as herein described. Preferred heteroaralkenyls contain a lower alkenyl moiety. An exemplary aralkenyl group is 4-pyridylvinyl, thienylethenyl, pyridylethenyl, imidazolylethenyl and pyrazinylethenyl.

"Heteroaralkyl" means a heteroaryl-alkyl-group wherein the heteroaryl and alkyl are as herein described. Preferred heteroaralkyls contain a lower alkyl moiety. Exemplary heteroaralkyl groups may contain thienylmethyl, pyridylmethyl, imidazolylmethyl and pyrazinylmethyl.

"Heteroaralkynyl" means an heteroaryl-alkynyl-group wherein the heteroaryl and alkynyl are as herein described. Preferred heteroaralkynyls contain a lower alkynyl moiety. Exemplary heteroaralkynyl groups are pyrid-3-ylacetylenyl and quinolin-3-ylacetylenyl and 4-pyridylethynyl.

"Heteroaroyl" means an means an heteroaryl-CO— group wherein the heteroaryl group is as herein described. Exemplary groups include thiophenoyl, nicotinoyl, pyrrol-2-ylcarbonyl and 1- and 2-naphthoyl and pyridinoyl.

"Heteroaryl" means an aromatic monocyclic or multicyclic ring system of about 5 to about 14 carbon atoms, preferably about 5 to about 10 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. The "heteroaryl" may also be substituted by one or more "ring system substituents" which may be the same or different, and are as defined herein. The designation of the aza, oxa or thia as a prefix before heteroaryl define that at least a nitrogen, oxygen or sulfur atom is present respectively as a ring atom. A nitrogen atom of an heteroaryl may be a basic nitrogen atom and may also be optionally oxidized to the corresponding N-oxide. Representative heteroaryl and substituted heteroaryl groups include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindole, 1,2,4-triazinyl and the like. Preferred heteroaryl groups include pyrazinyl, thienyl, pyridyl, pyrimidinyl, isoxazolyl and isothiazolyl.

"Heteroarylalkenyl" means a heteroaryl-alkenyl-group wherein the heteroaryl and alkenyl moieties are as described herein. Preferred heteroarylalkenyl groups contain a $C_{2-12}$ alkenyl moiety. Exemplary heteroarylalkenyl groups include pyridylpentenyl, pyridylhexenyl and pyridylheptenyl.

"Heteroarylalkynyl" means an aryl-alkynyl-group wherein the heteroaryl and alkynyl moiety are as herein described. Preferred heteroarylalkynyl groups contain a $C_{2-12}$ alkynyl moiety. Exemplary heteroarylalkynyl groups include 3-pyridyl-but-2-ynyl and pyridylpropynyl.

"Heteroaryldiazo" means an heteroaryl-azo-group wherein the heteroaryl and azo groups are as defined herein.

"Fused heteroarylcycloalkenyl" means a fused heteroaryl and cycloalkenyl as defined herein. Preferred fused heteroarylcycloalkenyls are those wherein the heteroaryl thereof is phenyl and the cycloalkenyl consists of about 5 to about 6 ring atoms. A fused heteroarylcycloalkenyl as a variable may be bonded through any atom of the ring system thereof capable of such. The designation of the aza, oxa or thia as a prefix before heteroaryl portion of the fused heteroarylcycloalkenyl define that at least a nitrogen, oxygen or sulfur atom is present respectively as a ring atom. The fused heteroarylcycloalkenyl may be optionally substituted by one or more ring system substituent, wherein the "ring system substituent" is as defined herein. The nitrogen atom of a fused heteroarylcycloalkenyl may be a basic nitrogen atom. The nitrogen atom of the heteroaryl portion of the fused heteroarylcycloalkenyl may also be optionally oxidized to the corresponding N-oxide. Representative fused heteroarylcycloalkenyl include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-dihydrobenzoxazolyl, and the like.

"Fused heteroarylcycloalkyl" means a fused heteroaryl and cycloalkyl as defined herein. Preferred fused heteroarylcycloalkyls are those wherein the heteroaryl thereof consists of about 5 to about 6 ring atoms and the cycloalkyl consists of about 5 to about 6 ring atoms. A fused heteroarylcycloalkyl as a variable may be bonded through any atom of the ring system thereof capable of such. The designation of the aza, oxa or thia as a prefix before heteroaryl portion of the fused heteroarylcycloalkyl define that at least a nitrogen, oxygen or sulfur atom is present respectively as a ring atom. The fused heteroarylcycloalkyl may be optionally substituted by one or more ring system substituent, wherein the "ring system substituent" is as defined herein. The nitrogen atom of a fused heteroarylcycloalkyl may be a basic nitrogen atom. The nitrogen atom of the heteroaryl portion of the fused heteroarylcycloalkyl may also be optionally oxidized to the corresponding N-oxide. Representative fused heteroarylcycloalkyl include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like.

"Fused heteroarylheterocyclenyl" means a fused heteroaryl and heterocyclenyl as defined herein. Preferred fused heteroarylheterocyclenyls are those wherein the heteroaryl thereof consists of about 5 to about 6 ring atoms and the heterocyclenyl consists of about 5 to about 6 ring atoms. A fused heteroarylheterocyclenyl as a variable may be bonded through any atom of the ring system thereof capable of such. The designation of the aza, oxa or thia as a prefix before the heteroaryl or heterocyclenyl portion of the fused heteroarylheterocyclenyl define that at least a nitrogen, oxygen or sulfur atom is present respectively as a ring atom. The fused heteroarylheterocyclenyl may be optionally substituted by one or more ring system substituent, wherein the "ring system substituent" is as defined herein. The nitrogen atom of a fused heteroarylazaheterocyclenyl may be a basic nitrogen atom. The nitrogen or sulphur atom of the heteroaryl portion of the fused heteroarylheterocyclyl may also be optionally oxidized to the corresponding N-oxide. The nitrogen or sulphur atom of the heteroaryl or heterocyclyl portion of the fused heteroarylheterocyclyl may also be optionally oxidized to the corresponding N-oxide, S-oxide or S,S-dioxide. Representative fused heteroarylheterocyclenyl include 7,8-dihydro[1,7]naphthyridinyl, 1,2-dihydro[2,7]naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, 1,2-dihydro-2,6-naphthyridinyl, and the like.

"Fused heteroarylheterocyclyl" means a fused heteroaryl and heterocyclyl as defined herein. Preferred fused heteroarylheterocyclyls are those wherein the heteroaryl thereof consists of about 5 to about 6 ring atoms and the heterocyclyl consists of about 5 to about 6 ring atoms. A fused heteroarylheterocyclyl as a variable may be bonded through any atom of the ring system thereof capable of such. The designation of the aza, oxa or thia as a prefix before the heteroaryl or heterocyclyl portion of the fused heteroarylheterocyclyl define that at least a nitrogen, oxygen or sulfur atom is present respectively as a ring atom. The fused heteroarylheterocyclyl may be optionally substituted by one or more ring system substituent, wherein the "ring system substituent" is as defined herein. The nitrogen atom of a fused heteroarylheterocyclyl may be a basic nitrogen atom. The nitrogen or sulphur atom of the heteroaryl portion of the fused heteroarylheterocyclyl may also be optionally oxidized to the corresponding N-oxide. The nitrogen or sulphur atom of the heteroaryl or heterocyclyl portion of the fused heteroarylheterocyclyl may also be optionally oxidized to the corresponding N-oxide, S-oxide or S,S-dioxide. Representative fused heteroarylheterocyclyl include 2,3-dihydro-1H pyrrol[3,4-b]quinolin-2-yl, 1,2,3,4-tetrahydrobenz[b][1,7]naphthyridin-2-yl, 1,2,3,4-tetrahydrobenz[b][1,6]naphthyridin-2-yl, 1,2,3,4-tetrahydro-9H-pyrido[3,4-b]indol-2yl, 1,2,3,4-tetrahydro-9H-pyrido[4,3-b]indol-2yl, 2,3,-dihydro-1H-pyrrolo[3,4-b]indol-2-yl, 1H-2,3,4,5-tetrahydroazepino[3,4-b]indol-2-yl, 1H-2,3,4,5-tetrahydroazepino[4,3-b]indol-3-yl, 1H-2,3,4,5-tetrahydroazepino[4,5-b]indol-2 yl, 5,6,7,8-tetrahydro-[1,7]napthyridinyl, 1,2,3,4-tetrhydro[2,7]naphthyridyl, 2,3-dihydro[1,4]dioxino[2,3-b]pyridyl, 2,3-dihydro[1,4]dioxino[2,3-b]pryidyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]napthyridinyl, 1,2,3,4-tetrahydro[1,6]napthyridinyl, 1,2,3,4-tetrahydro[1, 7]napthyridinyl, 1,2,3,4-tetra-hydro[1,8]napthyridinyl, 1,2,3,4-tetrahydro[2,6]napthyridinyl, and the like.

"Heterocyclenyl" means a non-aromatic monocyclic or multicyclic hydrocarbon ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Preferred ring sizes of the individual rings of the ring system include about 5 to about 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or more ring system substituent, wherein the "ring system substituent" is as defined herein. The nitrogen atom of an heterocyclenyl may be a basic nitrogen atom. The nitrogen or sulphur atom of the heterocyclenyl may also be optionally oxidized to the corresponding N-oxide, S-oxide or S,S-dioxide. Representative monocyclic heterocyclenyl groups include 3,4-dihydro-2H-pyran, tetrahydrothiophenyl. Particular representative monocyclic azaheterocyclenyl groups include 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, tetrahydrothiopyranyl, and the like.

"Heterocyclyl" means a non-aromatic saturated monocyclic or multicyclic ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more "ring system substituents" which may be the same or different, and are as defined herein. The nitrogen atom of an heterocyclyl may be a basic nitrogen atom. The nitrogen or sulphur atom of the heterocyclyl may also be optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. Preferred heterocyclyl group substituents include amidino, halogen, hydroxy, alkoxycarbonylalkyl, carboxyalkyl or $Y^1Y^2N-$ as defined herein.

"Hydrate" means a solvate wherein the solvent molecule(s) is/are $H_2O$.

"Hydroxyalkyl" means a HO-alkyl-group wherein alkyl is as herein defined. Preferred hydroxyalkyls contain lower alkyl. Exemplary hydroxyalkyl groups include hydroxymethyl and 2-hydroxyethyl.

"Modulate" means the ability of a compound to either directly (by binding to the receptor as a ligand) or indirectly (as a precursor for a ligand or an inducer which promotes production of a ligand from a precursor) induce expression of gene(s) maintained under hormone control, or to repress expression of gene (s) maintained under such control.

"N-oxide" means a moiety of the following structure

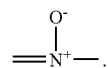

"Patient" includes both human and other mammals.

"Pharmaceutically acceptable cation" means those base addition salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable cations are well known in the art. For example, S. M Berge, et al. describe pharmaceutically acceptable salts in detail in J. Pharmaceutical Sciences, 1977, 66: p.1-19. Representative pharmaceutically acceptable cations include alkali or alkaline earth metal cations such as sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

"Pharmaceutically acceptable ester" means an ester which hydrolyzes in vivo and include that which breaks down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates and ethylsuccinates.

"Pharmaceutically acceptable prodrugs" as used herein means those prodrugs of the compounds of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds of this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology,. K. Widder et al, Ed., Academic Press, 42, p.309-396, 1985; A Textbook of Drug Design and Developement, Krogsgaard-Larsen and H. Bundgaard, ed., Chapter 5; "Design and Applications of Prodrugs" p.113-191, 1991; Advanced Drug Delivery Reviews, H. Bundgard, 8, p.1-38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference.

"Optionally substituted tetrazolyl" means a group of formula

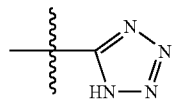

wherein the hydrogen atom thereof may be substituted by alkyl, carboxyalkyl or carbalkoxyalkyl.

"Ring system substituents" mean substituents attached to aromatic or nonaromatic ring systems inclusive of hydrogen, alkyl, aryl, heteroaryl, aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, aryldiazo, heteroaryldiazo, amidino, $Y^1Y^2N-$, $Y^1Y^2N$-alkyl-, $Y^1Y^2NCO-$ or $Y^1Y^2N\,SO_2-$, wherein $Y^1$ and $Y^2$ are independently hydrogen, optionally substituted alkyl, optionally substituted aryl, optionally substituted aralkyl or optionally substituted heteroaralkyl, or for where the substituent is $Y^1Y^2N-$, $Y^1Y^2N$-alkyl-, then one of $Y^1$ and $Y^2$ may be acyl or aroyl as defined herein and the other of $Y^1$ and $Y^2$ is as defined previously, or for where the substituent is $Y^1Y^2NCO-$ or $Y^1Y^2NSO_2$, $Y^1$ and $Y^2$ may also be taken together with the N atom through which $Y^1$ and $Y^2$ are linked to form a 4 to 7 membered heterocyclyl or heterocyclenyl. When a ring system is saturated or partially saturated, the "ring system substituents" further include, methylene ($H_2C=$), oxo ($O=$), thioxo ($S=$). Ring system substituents encompassing a basic nitrogen atom include optionally substituted amidino, optionally substituted imino, and optionally substituted amine groups.

"Solvate" means a physical association of a compound of this invention with one or more solvent molecules. This physical association involves varying degrees of ionic and covalent bonding, including hydrogen bonding. In certain instances the solvate will be capable of isolation, for example when one or more-solvent molecules are incorporated in the crystal lattice of the crystalline solid. "Solvate" encompasses both solution-phase and isolable solvates. Representative solvates include ethanolates, methanolates, and the like.

"$Y^1Y^2N-$" means a substituted or unsubstituted amino group, wherein $Y^1$ and $Y^2$ are as herein described. Exemplary groups include amino ($H_2N-$), methylamino, dimethylamino, diethylamino, pyrrolidine, piperidine, benzylamino, or phenethylamino.

"$Y^1Y^2NCO-$" means a substituted or unsubstituted carbamoyl group, wherein $Y^1$ and $Y^2$ are as herein described. Exemplary groups are carbamoyl ($H_2NCO-$) and dimethylaminocarbamoyl ($Me_2NCO-$).

"$Y^1Y^2NSO_2-$" means a substituted or unsubstituted sulfamoyl group, wherein Yand $Y^2$ are as herein described. Exemplary groups are aminosulfamoyl ($H_2NSO_2-$) and dimethylaminosulfamoyl ($Me_2NSO_2-$).

In a specific embodiment, the term "about" or "approximately" means within 20%, preferably within 10%, and more preferably within 5% of a given value or range.

As used herein the following reagents, solvents and terms are identified by the abbreviations indicated:

Acetic acid (AcOH or HOAc); acetic anhydride ($Ac_2O$); acetamidomethyl (Acm); benzyl (Bn); t-Butoxycarbonyl (Boc); 2-(4-Biphenylyl)-prop-2-yl 4'-methoxycarbonylphenyl carbonate (Bpoc); benzyl carbamate (CBZ); n-butyl lithium (n-BuLi), cerium ammonium nitrate (CAN); cyclopropyl (Cp); 1,5-diazabicyclo[4.3.0]nona-5-ene (DBN); 1,8-diazabicyclo[5.4.0]undec-7-ene (DBU); dichloromethane (DCM); diethylazodicarboxylate (DEAD); dicyclohexilcarbodiimide (DCC); diisobutylaluminum hydride (DIBAL); N,N-Diisopropylcarbodiimide (DIC), diisopropylethylamine (DIEA); N,N-dimethylaniline (DMA); 1,2-Dimethoxyethane (DME); N,N-dimethylformamide (DMF); diethyl azodicarboxylate (DEAD); 4-dimethylaminopyridine (DMAP); 1,3-dimethyl-3,4,5,6-tetrahydro-2(1H)-pyrimidinone (DMPU); dimethylsulfoxide (DMSO); N-ethyloxycarbony-2-ethyloxy-1,2-dihydroquinone (EEDQ), equivalent (eq.); ethyl (Et); ethanol (EtOH); diethyl ether ($Et_2O$); triethylamine ($Et_3N$); ethyl acetate (EtOAc); 1-(3-dimethylaminopropyl)-3-ethyl-carbodiimide-hydrochloride (EDC); hexamethylphosphoramide (HMPA); fast atom bombardment (FAB); 2-furanmethyloxycarbonyl (Foc), acetic acid (HOAc); high-performance liquid chromatography (HPLC); di-isopropylethylamine (Hunigs base); O-(7-azabenzotriazol-1-yl-1,1,3,3-tetramethylur onium hexafluorophosphate (HATU); O-(7-azabenzotriazol-1-yl-1,1,3,3-bis(tetramethylene uronium hexafluorphosphate (HApyU), O-(7-azabenzotriazol-1-yl)-1,1,3,3-bis (pentamethylene)uronium hexafluorophosphate (HApipU),O-(7-azabenzotrizol-1-yl)-1,3-dimethyl-1,3-trimethylene uronium hexafluorophosphate (HAMTU); iso-propylacetate (iPrOAc); O-benzotriazolyl-1-yl-1,1,3, 3-tetramethyluronium hexafluorophosphate(HBTU); 1-Hydroxybenzotriazole hydrate (HOBT); iso-propanol (iPrOH); potassium bis(trimethylsilyl)amide (KHMDS); lithium bis(trimethylsilyl)amide (LHMDS); methyl (Me); methanol (MeOH); m-chloroperoxybenzoic acid (MCPBA); methanesulfonyl chloride (mesyl chloride or MsCl); p-ethoxybenzyloxycarbonyl (Moz); sodium bis (trimethylsilyl)amide (NaHMDS); N-methylpyrrolidine (NMP); phenyl (Ph); Pyridine (Py); room temperature (r.t.); t-butyl methyl ether (TBME); benzotriazolyl-yl-1, 1,3,3-bis (tetramethylene uronium tetrafluoroborate) (TBTU); 2-(trimethylsilyl)ethyl carbonate(TEOC); tetrahydrofuran (THF); trifluoroacetic acid (TFA); tetramethylethylene diamine (TMEDA); trimethylsilane (TMS); p-toluenesulfonyl chloride (tosyl chloride or TsCl); trityl (Trt), and p-toluenesulfonic acid (p-TSA).

PREFERRED EMBODIMENTS

A preferred embodiment of the invention is a method for treating a disease state in a patient, associated with a detrimental excess of Factor Xa activity, comprising administering to said patient a pharmaceutically effective amount of the compound of formula I, or a pharmaceutically acceptable salt thereof.

Another preferred aspect of the invention is the compound of formula I wherein $R^1$ is hydrogen, $-CO_2R^3$, $-C(O)R^3$, $-CH_2OR^4$ or $-CH_2SR^4$.

Another preferred aspect of the invention is the compound of formula I wherein $R^1$ is hydrogen, $-CO_2R^3$, $-CH_2OR^4$ or $-CH_2SR^4$; more preferred is wherein $R^1$ is hydrogen, $-CO^2R^3$ or $-CH_2OR^4$.

Another preferred aspect of the invention is the compound of formula I wherein $R^1$ is —$CO_2R^3$ and $R^3$ is lower alkyl or hydrogen.

Another preferred aspect of the invention is the compound of formula I wherein $R^1$ is —$CH_2OR^4$ or —$CH_2SR^4$ and $R^4$ is hydrogen or lower alkyl.

Another preferred aspect of the invention is the compound of formula I wherein $R^1$ is hydrogen; and ----- is a double bond.

Another preferred aspect of the invention is the compound of formula I wherein $R^1$ is —$CO_2R^3$ and $R^3$ is lower alkyl or hydrogen, and ----- is a single bond Another preferred aspect of the invention is the compound of formula I wherein Ring A is an optionally substituted 5 membered azaheterocyclyl ring or an optionally substituted 5 membered azaheterocyclenyl ring.

Another preferred aspect of the invention is the compound of formula I wherein Ring A is an optionally substituted pyrrolidinyl ring or an optionally substituted pyrrolinyl ring.

Another preferred aspect of the invention is the compound of formula I wherein $R^2$ is optionally substituted cycloalkyl, optionally substituted cycloalkenyl, optionally substituted heteroaryl, optionally substituted fused arylcycloalkyl, optionally substituted fused arylcycloalkyl, optionally substituted fused arylcycloalkenyl, optionally substituted fused arylheteroaryl, optionally substituted fused heteroarylaryl, optionally substituted fused heteroarylcycloalkyl, optionally substituted fused heteroarylcycloalkenyl, optionally substituted fused heteroarylheterocyclyl, optionally substituted fused heteroarylheterocyclenyl.

Another preferred aspect of the invention is the compound of formula I wherein $R^2$ is optionally substituted cycloalkyl, optionally substituted heterocyclyl, optionally substituted aryl, optionally substituted heteroaryl, optionally substituted aralkyl or optionally substituted aralkynyl.

Another preferred aspect of the invention is the compound of formula I wherein $R^2$ is optionally substituted phenyl, optionally substituted naphthyl, or optionally substituted heteroaryl.

Another preferred aspect of the invention is the compound of formula I wherein $R^2$ is optionally substituted (phenyl substituted phenyl), optionally substituted (heteroaryl substituted phenyl), optionally substituted (phenyl substituted heteroaryl), optionally substituted (heteroaryl substituted heteroaryl), optionally substituted (phenyl substituted heterocyclenyl), optionally substituted (phenyl substituted heterocyclyl), optionally substituted (heteroaryl substituted heterocyclenyl) or optionally substituted (heteroaryl substituted heterocyclyl), (wherein the term "optionally substituted" before the term in the parenthesis, denote that the phenyl, heteroaryl, heterocyclyl or heterocyclenyl portions thereof could be further substituted as noted per their definitions).

Another preferred aspect of the invention is the compound of formula I wherein $R^2$ is phenyl, biphenyl, naphthyl, phenyl or heterobiphenyl.

Another preferred aspect of the invention is the compound of formula I wherein $R^3$ is lower alkyl.

Another preferred aspect of the invention is the compound of formula I wherein $R^4$ is hydrogen or lower alkyl.

Another preferred aspect of the invention is the compound of formula I wherein $Z^1$ is optionally substituted azaheteroaryl, optionally substituted azaheterocyclyl, optionally substituted azaheterocyclenyl, optionally substituted fused azaheteroarylcycloalkyl, optionally substituted fused azaheteroarylcycloalkenyl, optionally substituted fused azaheteroarylheterocyclyl, optionally substituted fused azaheteroarylheterocyclenyl, optionally substituted fused azaheteroarylazaheterocyclyl, optionally substituted fused azaheteroarylazaheterocyclenyl.

Another preferred aspect of the invention is the compound of formula I wherein $Z^1$ is optionally substituted dihydropyridine, optionally substituted tetrahydropyridine, optionally substituted optionally substituted piperidine, optionally substituted quinolinyl, optionally substituted isoquinolinyl, optionally substituted indolyl, optionally substituted benzothiophenyl, optionally substituted or optionally substituted azaindolyl.

Another preferred aspect of the invention is the compound of formula I wherein $Z^1$ is phenyl substituted by, at least, an amidino substituent.

Another preferred aspect of the invention is the compound of formula I wherein $Z^1$ is substituted by, at least, $Y^1Y^2N$— or $Y^1Y^2N$-alkyl-.

Another preferred aspect of the invention is the compound of formula I wherein $Z^1$ is substituted by, at least, a moiety of the formula

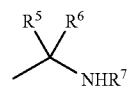

wherein $R^7$ is hydrogen, and $R^5$ and $R^6$ are hydrogen or together are =$NR^8$, and $R^8$ is selected from hydrogen, $R^9O_2C$—, $R^9O$—, $HO$—, $R^9C(O)$—, $HCO$—, cyano, optionally substituted lower alkyl, nitro or $Y^{1a}Y^{2a}N$—; wherein $R^9$ is alkyl, optionally substituted aralkyl, or optionally substituted heteroaralkyl, and $Y^{1a}$ and $Y^{2a}$ are independently hydrogen or alkyl.

Another preferred aspect of the invention is the compound of formula I wherein $Z^1$ is substituted by, at least, an amidino group.

Another preferred aspect of the invention is the compound of formula I wherein $Z^1$ is substituted by, at least, an amidino group of the formula

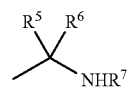

wherein $R^5$ and $R^6$ together are =$NR^8$, and $R^8$ is hydrogen.

Another preferred aspect of the invention is the compound of formula I wherein $Z^1$ is substituted azaheterocyclyl or substituted azaheterocyclenyl; and at least one of the ring system substituents of the substituted azaheterocyclyl or substituted azaheterocyclenyl is an amidino group.

Another preferred aspect of the invention is the compound of formula I wherein $Z^1$ is substituted by, at least, an amidino group in the meta or para position of the ring system of $Z^1$, relative to the position of attachment of $Z^1$ to the rest of the molecule.

Another preferred aspect of the invention is the compound of formula I wherein $Z^1$ is substituted by, at least, an amidino group in the meta position of the ring system of $Z^1$, relative to the position of attachment of $Z^1$ to the rest of the molecule; and $Z^1$ is also substituted by a hydroxyl group in the para position to said amidino group.

Another preferred aspect of the invention is the compound of formula I wherein $Z^1$ is substituted by a moiety of the formula

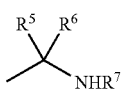

wherein R7 is hydrogen, and $R^5$ and $R^6$ together are hydrogen.

Another preferred aspect of the invention is the compound of formula I wherein $Z^1$ is substituted by a moiety of the formula

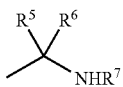

wherein $R^7$ is hydrogen.

Another preferred aspect of the invention is the compound of formula I wherein $Z^1$ is substituted by a moiety of the formula

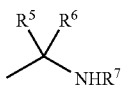

wherein $R^5$ and $R^6$ are =$NR^8$, and $R^8$ is selected from hydrogen, $R^9O_2C$—, $R^9O$—, HO—, $R^9C(O)$—, wherein $R^9$ is lower alkyl.

Another preferred aspect of the invention is the compound of formula I wherein ----- is a single bond and $R^7$ are hydrogen.

Species according to the invention are selected from the following:

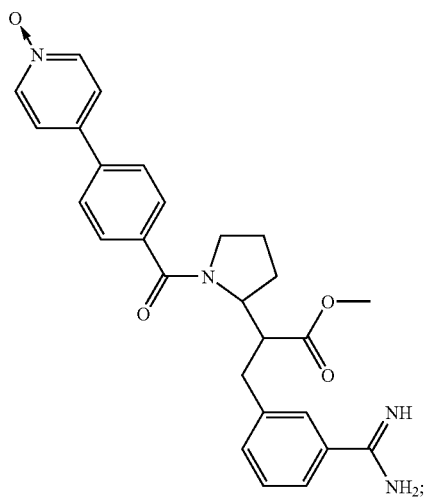

-continued

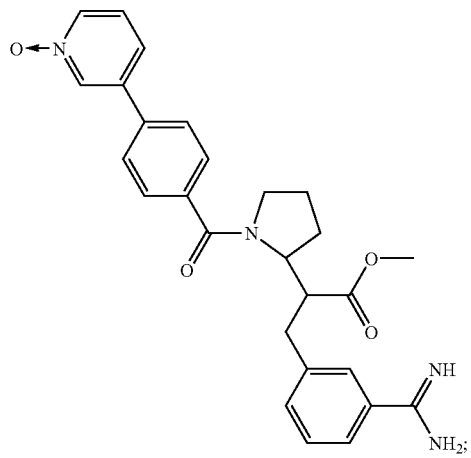

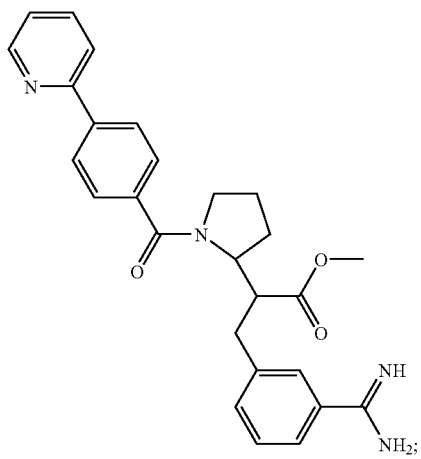

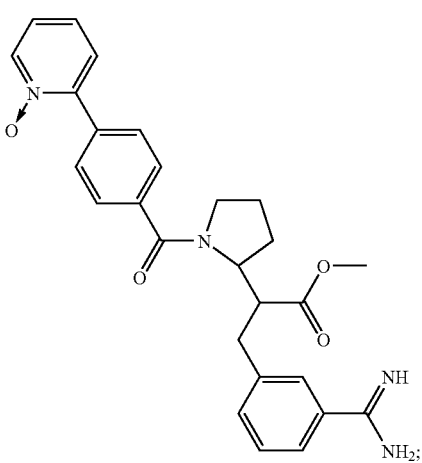

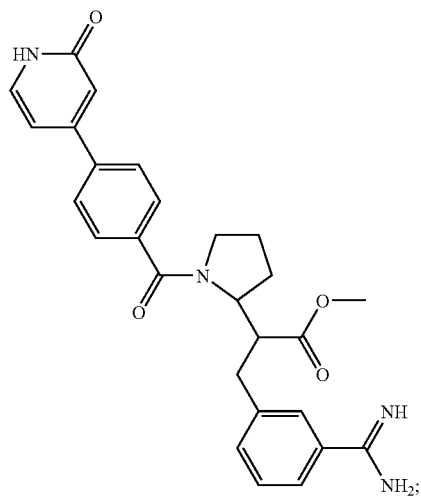
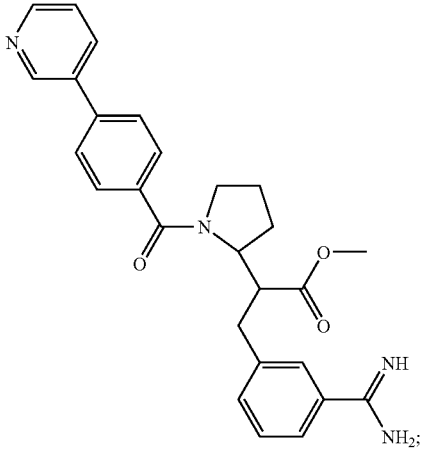
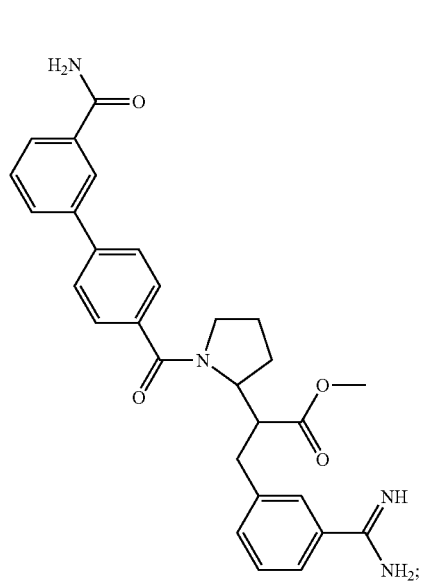
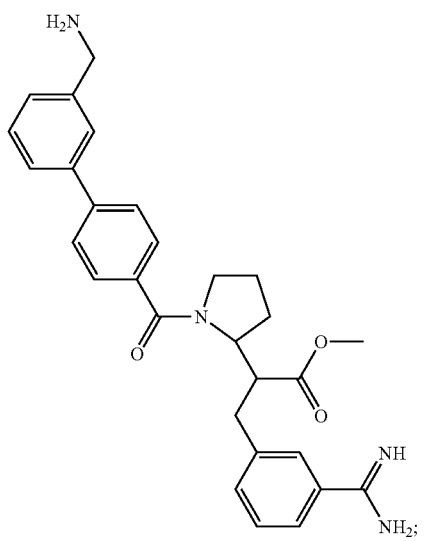
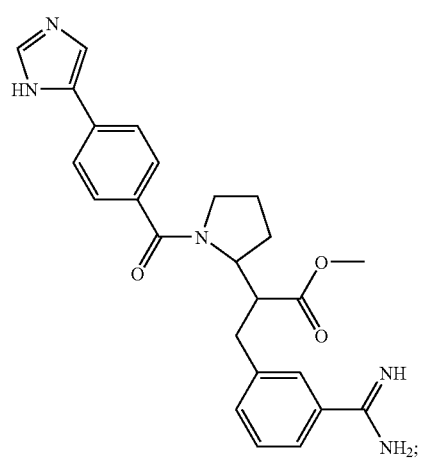
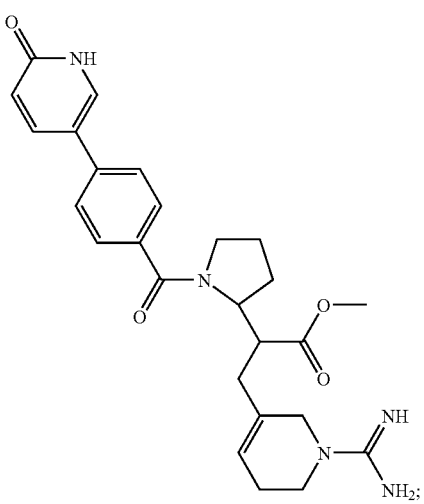

-continued
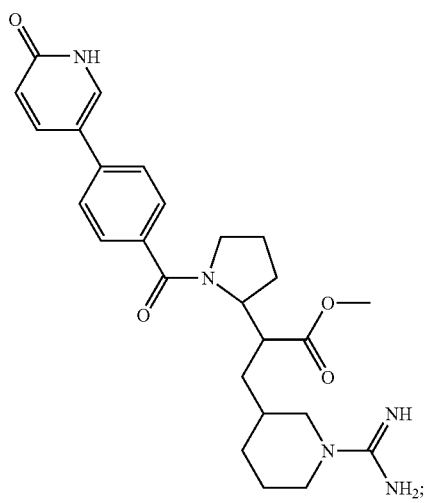
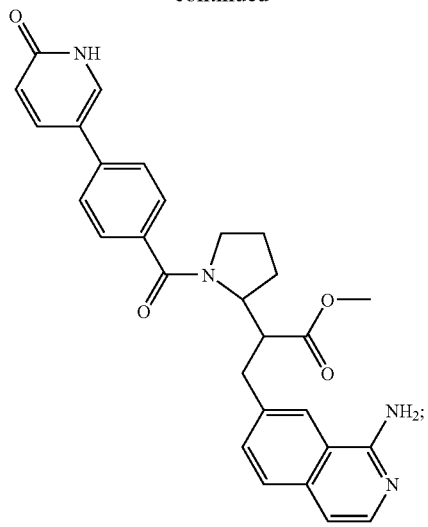
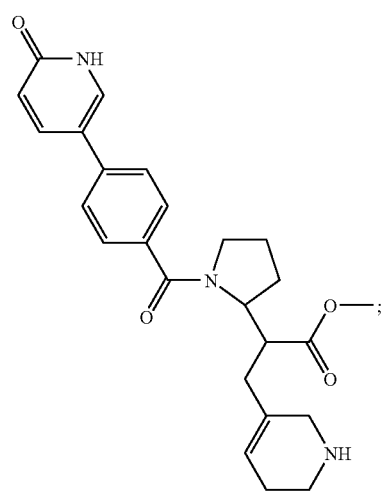
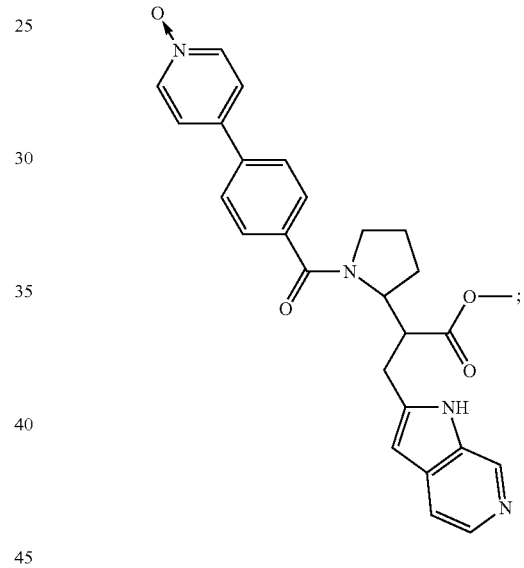
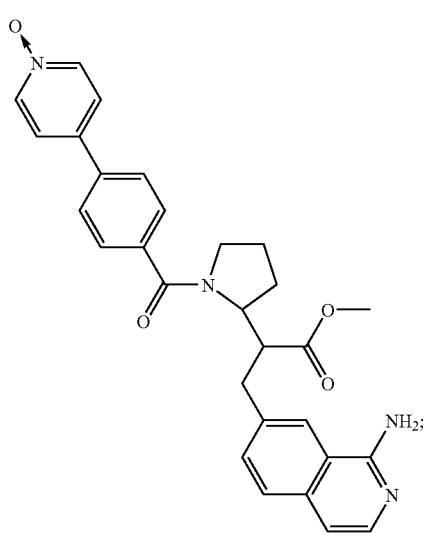
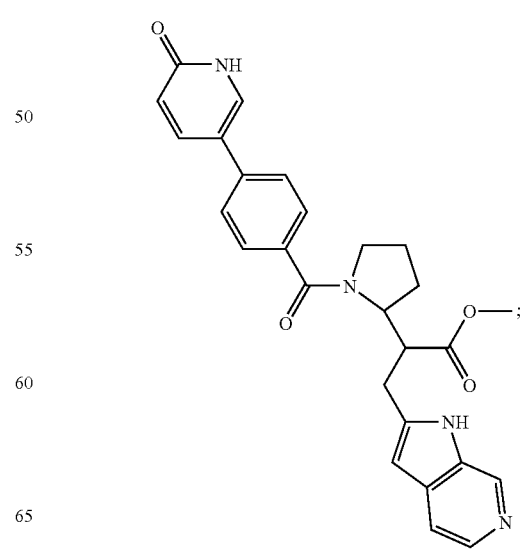

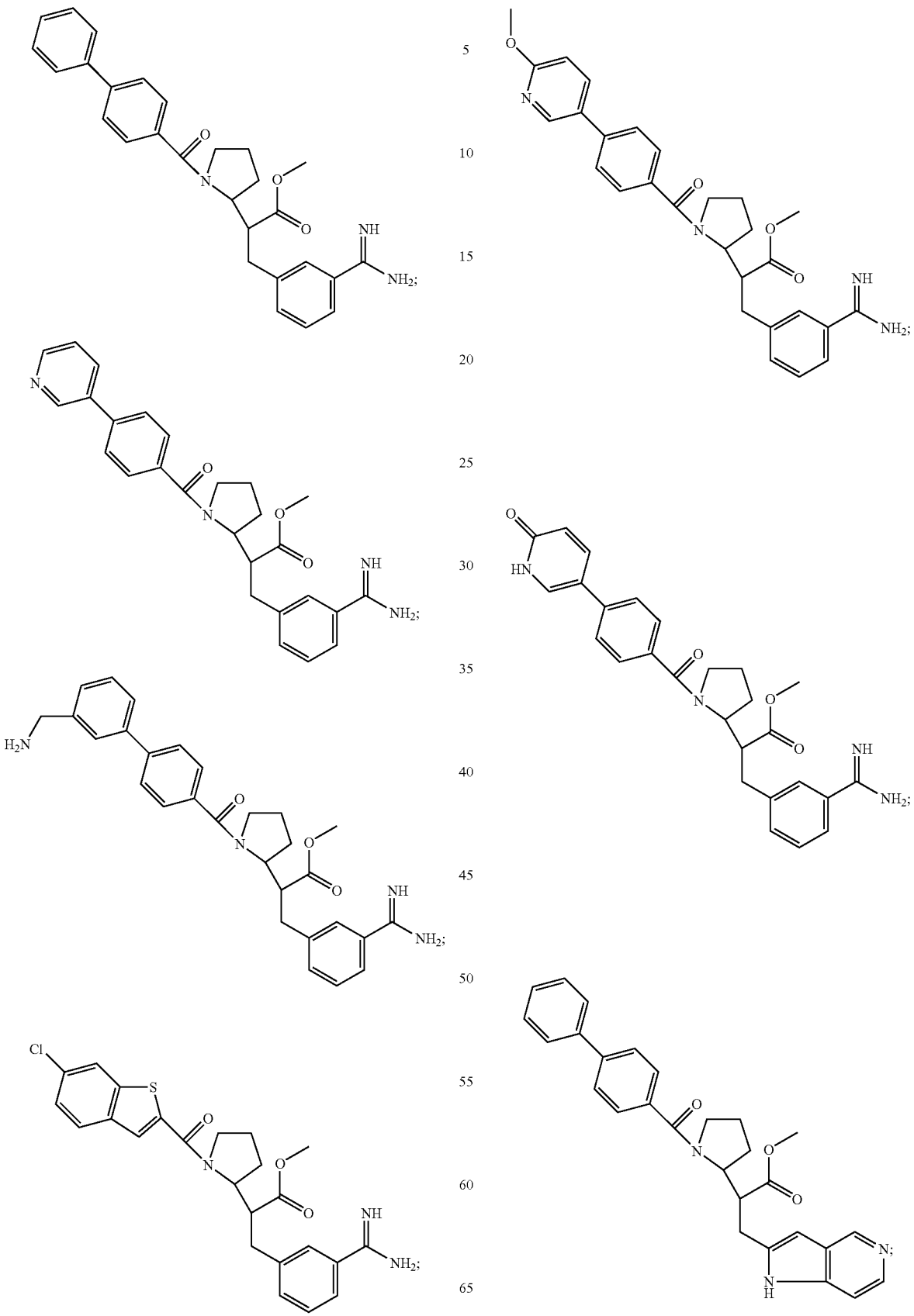

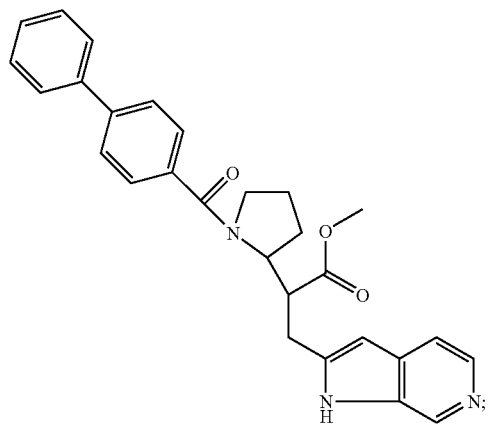
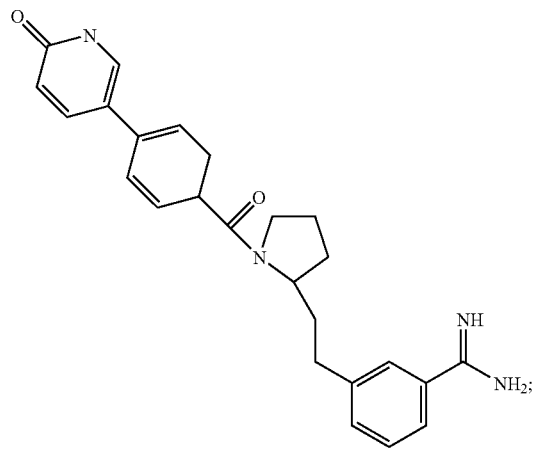
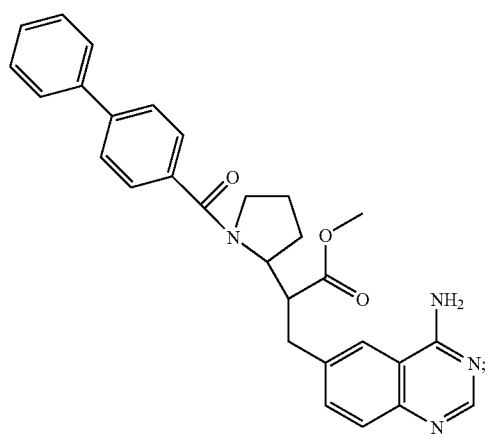
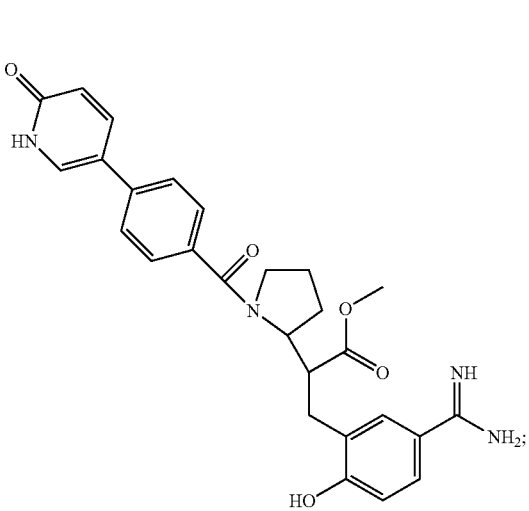
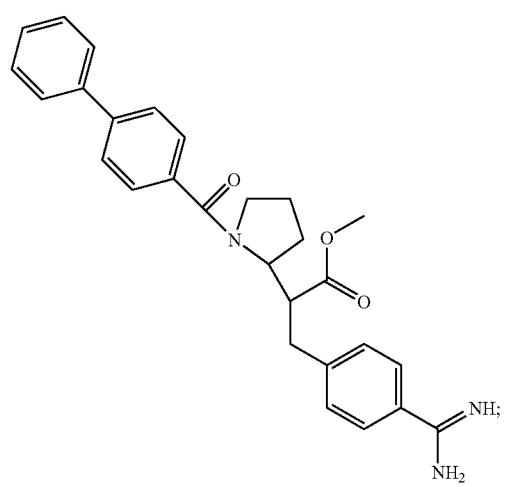

-continued
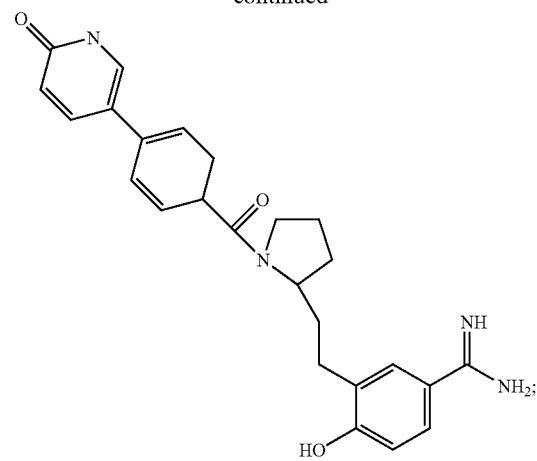
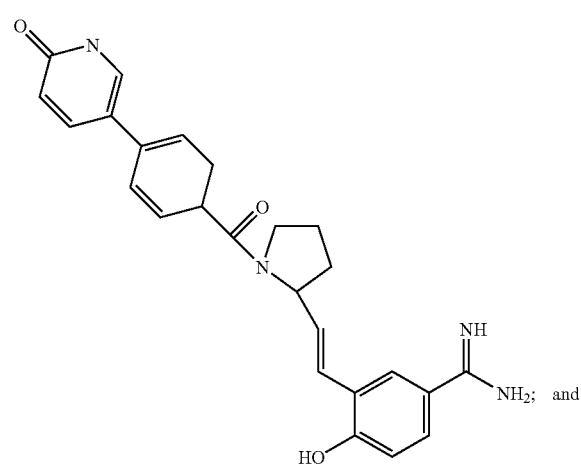
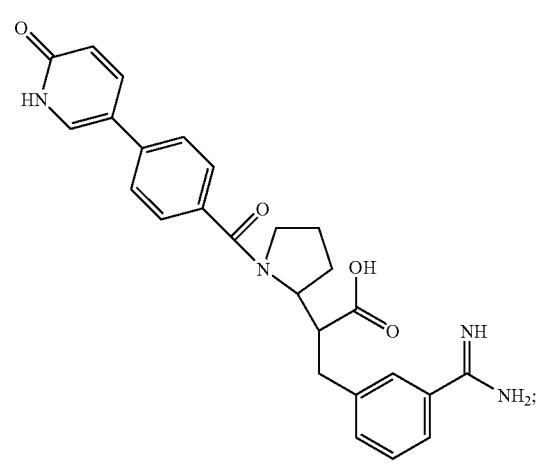
or a pharmaceutically acceptable salt thereof, an N-oxide thereof, a solvate thereof, an acid bioisostere thereof, or prodrug thereof.
Preferred species are selected from the following:
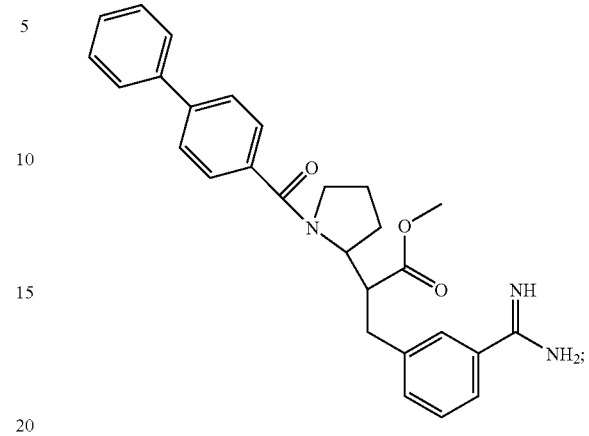
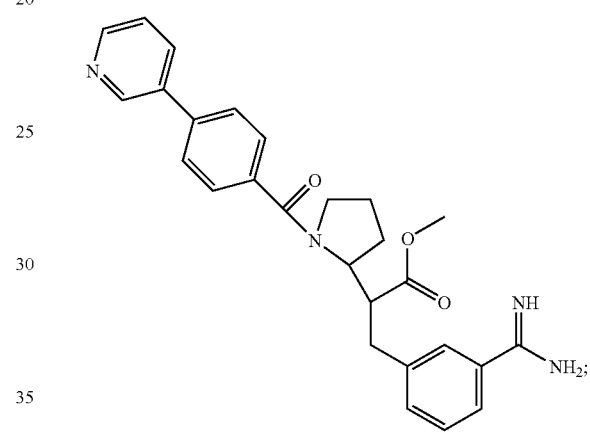
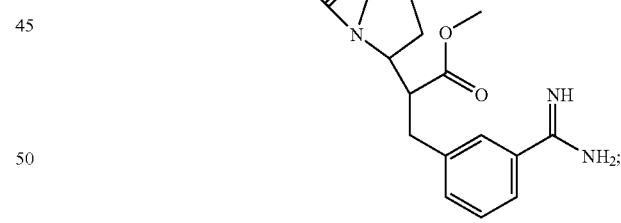

-continued
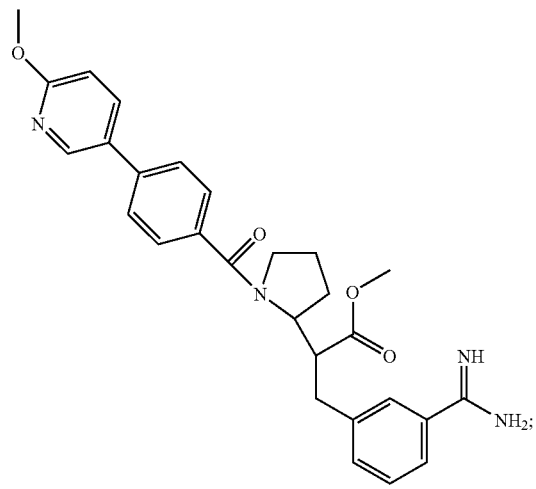
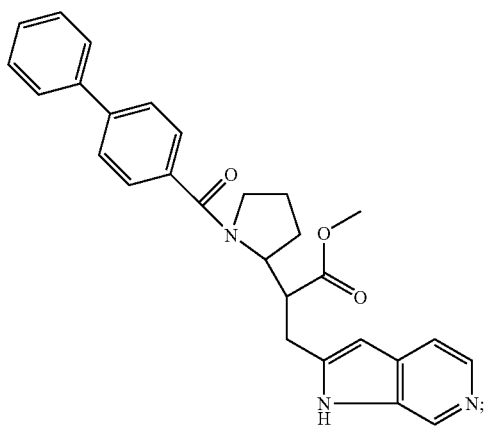
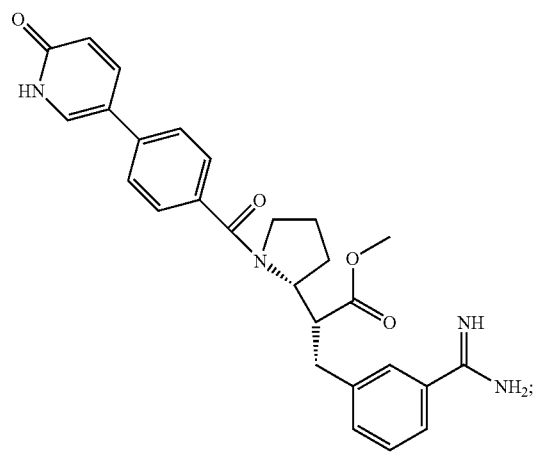
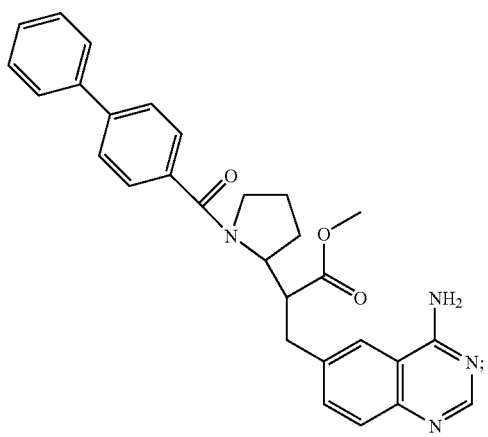
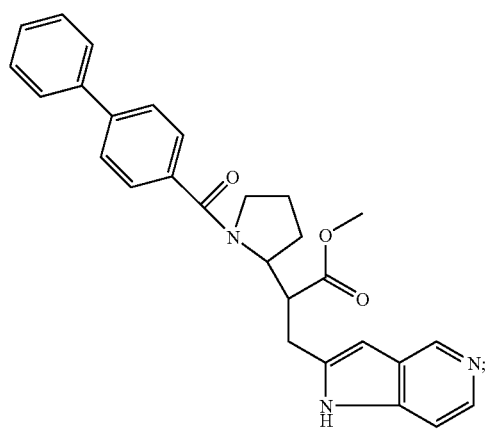
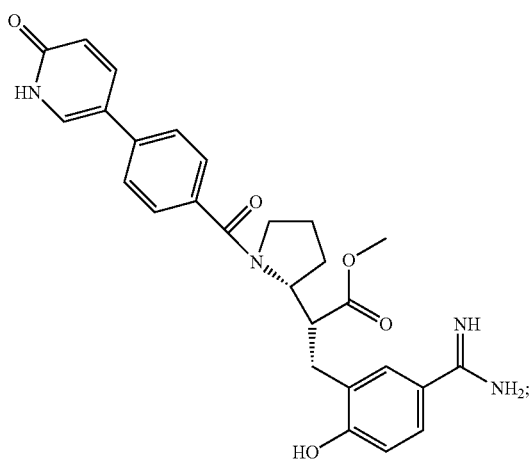

-continued
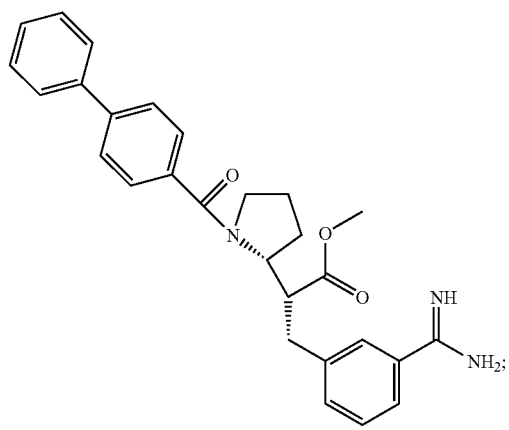
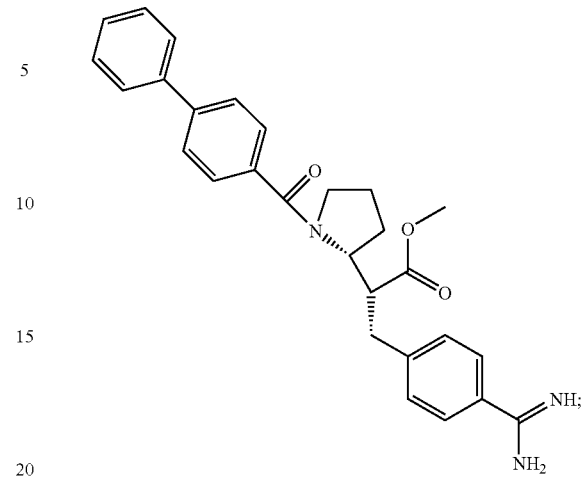
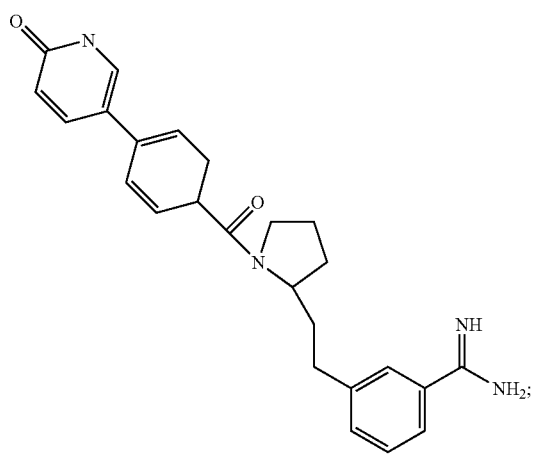
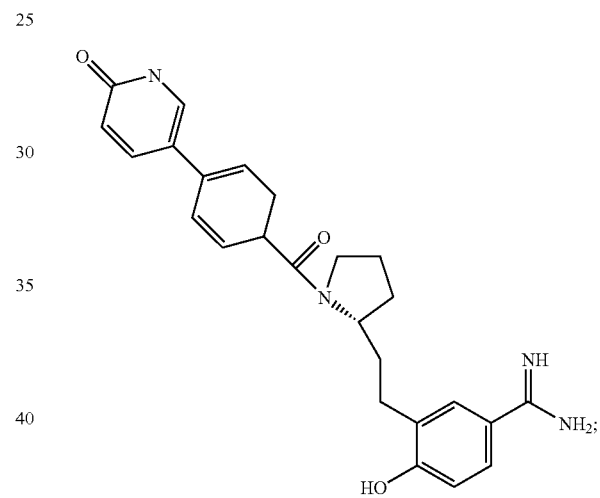
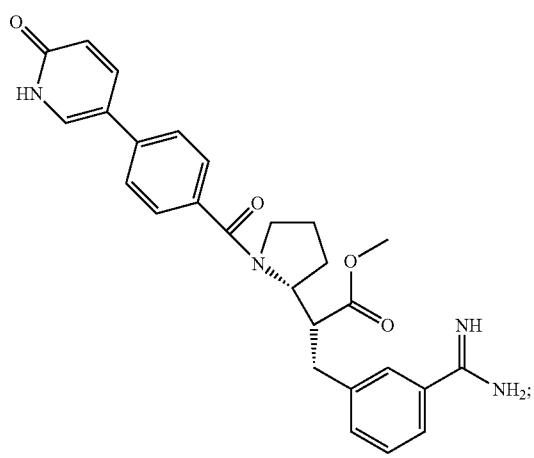
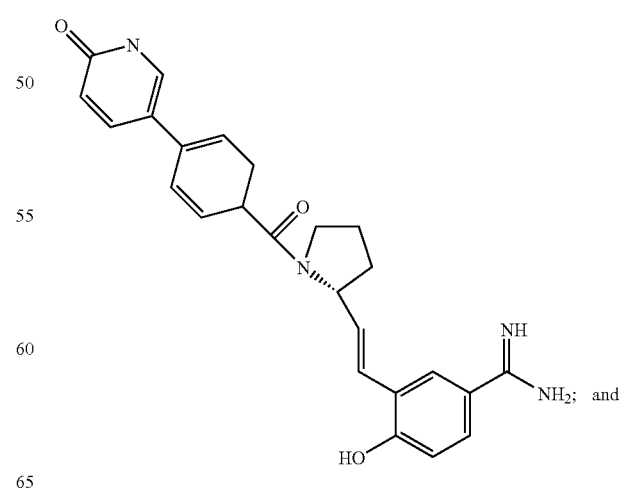
and

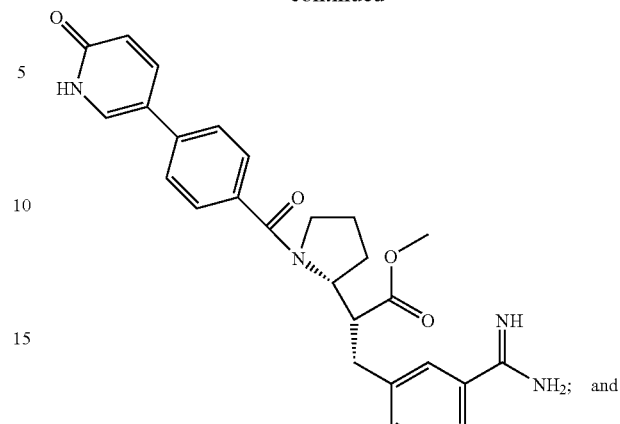

or a pharmaceutically acceptable salt thereof, an N-oxide thereof, a solvate thereof, an acid bioisostere thereof, or prodrug thereof.

More preferred species are selected from the following:

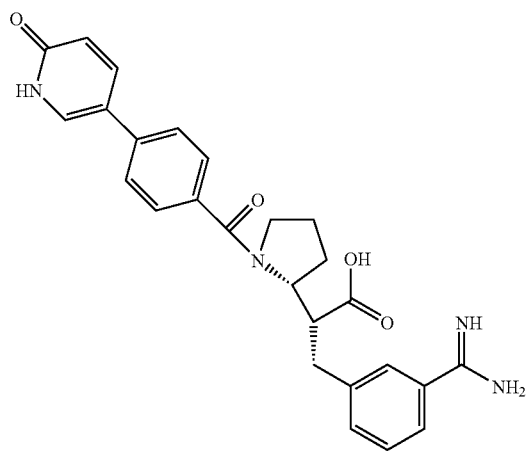

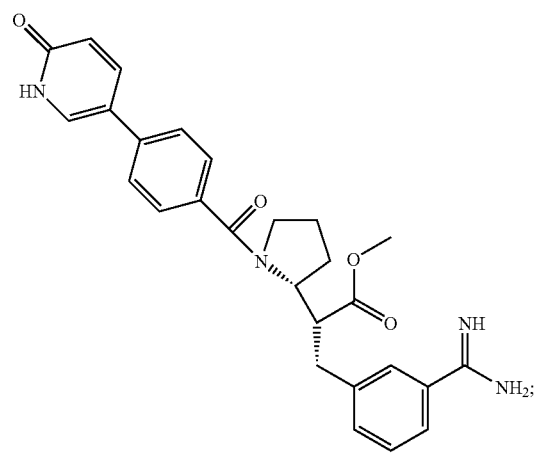

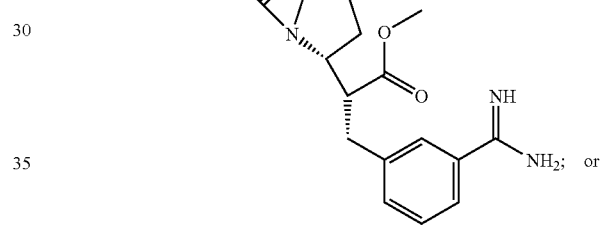

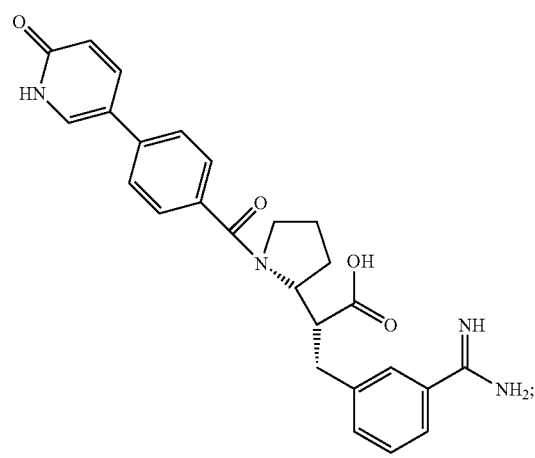

a pharmaceutically acceptable salt thereof, an N-oxide thereof, a solvate thereof, an acid bioisostere thereof, or prodrug thereof.

This invention also encompasses all combinations of preferred aspects of the invention noted herein.

Compounds of Formula I may be prepared by the application or adaptation of known methods, by which is meant methods used heretofore or described in the literature, or by methods according to this invention herein.

Compounds of formula (III)

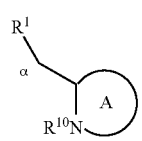

wherein $R^1$ is —$CO_2R^3$, —$C(O)R^3$, or —$CH_2OR^4$; $R^3$ and $R^4$ are independently a hydrogen atom of an alkyl group; ring A is as hereinbefore defined and $R^{10}$ is an appropriate amine protecting group, may be prepared by conversion of the corresponding amine protected a-amino compound of formula (II)

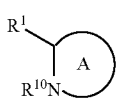 (II)

wherein $R^1$ is COOH, ring A and $R^{10}$ are as hereinbefore defined, by a method known as the Arndt-Eistert synthesis (See J March, Advanced Organic Chemistry, 3rd ed., Wiley Intersciences; Meier et al., Angew. Chem. Int. Ed. Engl. 14, p.32-43, 1975). For example, by converting $R^1$ to the acyl halide, and then reacting it with diazomethane, or the like, in an appropriate solvent to form the diazoketone derivative. Treatment of the diazoketone derivative with water (or alcohol) and silveroxide, or the like, affords the compound of formula (III), wherein $R^1$ is $COOR^3$, and $R^3$ is hydrogen or lower alkyl.

The compound of formula (IV)

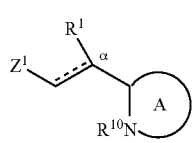 (IV)

wherein $Z^1$, ring A and $R^{10}$ are as hereinbefore defined, $R^1$ is $CO_2R^3$, wherein $R^3$ is lower alkyl; and

----- is a single bond, by deprotonating the compound (III) at the α-position with an appropriate base, followed by alkylation with an appropriate alkyl halide $Z^1CH_2$—X, wherein $Z^1$ is as hereinbefore defined.

The compound of formula (V)

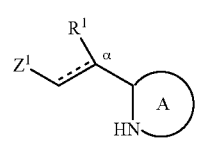 (V)

wherein $Z^1$, $R^1$, ring A is as hereinbefore defined; and

----- is a single bond, may be synthesized by selectively removing the amino protecting group $R^{10}$ of the compound of formula (IV) using known procedures for deprotecting amino groups. For example, wherein $R^{10}$ is an acid labile amino protecting group (e.g. tert-butoxycarbonyl (BOC)) the amino protecting group may be removed by treatment with acid.

Alternatively, if the amine protected derivative (III) (i.e. $R^{10}$ is a protecting group) is used in the alkylation step, subsequent selective deprotection is required after the alkylation step to afford the intermediate (V). This deprotection step can be carried out using known procedures for deprotecting amino groups. For example, wherein $R^{10}$ is an acid labile amino protecting group (e.g. tert-butoxycarbonyl (BOC)) the amino protecting group may be removed by treatment with acid.

The amide compound of formula (VII)

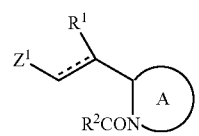 (VII)

wherein

----- is a single or double bond, $Z^1$, $R^1$, ring A and $R^2$ are as hereinbefore defined, may be synthesized by reacting a compound of formula (V) with a compound of formula (VI)

$$R^2—COOH \qquad (VI)$$

wherein $R^2$ is as hereinbefore defined, under standard peptide coupling procedures such as treatment with a carbodiimide, for example dicyclohexylcarbodiimide, or 2-(1H-benzotriazol-1-yl)-1,1,3,3-tetramethyluronium tetrafluoroborate, in the presence of a base, for example, triethylamine, in an inert solvent such as dichloromethane, DMF or tetrahydrofuran and at a temperature at about room temperature. An additional deprotection step may be required for compounds wherein $R^2$ contains an reactive functional group which is protected prior to the coupling step.

The compound of formula (VII) wherein $R^1$, ring A and $R^2$ are as hereinbefore defined;

----- is a single or double bond; and $Z^1$ is substituted azaheteroaryl, substituted azaheterocyclyl, substituted azaheterocyclenyl, substituted fused azaheteroarylcycloalkyl, substituted fused azaheteroarylcycloalkenyl, substituted fused azaheteroarylheterocyclyl, substituted fused azaheteroarylheterocyclenyl, substituted fused azaheteroarylazaheterocyclyl, substituted fused azaheteroarylazaheterocyclenyl wherein at least one nitrogen atom incorporated in the ring system of $Z^1$ is substituted by

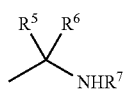

wherein $R^5$, $R^6$ are $=NR^8$, and $R^7$ and $R^8$ is as herein before defined, may be synthesized by reacting a compound of formula (VII) wherein $Z^1$ is substituted aryl, substituted cycloalkyl, substituted cycloalkenyl, optionally substituted heteroaryl, optionally substituted heterocyclyl, substituted heterocyclenyl, substituted fused arylcycloalkyl, substituted fused arylcycloalkenyl, substituted fused heteroarylcycloalkyl, optionally substituted fused heteroarylcycloalkenyl, substituted fused heteroarylheterocyclyl, substituted fused heteroarylheterocyclenyl, wherein one of the ring substituents of $Z^1$ is cyano, with $H_2S$, pyridine, triethylamine; followed by reacting with MeI and $NH_4OAc$ in MeOH at 60° C., or HCl and MeOH at 60° C.; followed by $NH_3$ and MeOH at 60° C.

A compound of formula (1) wherein $Z^1$, $R^2$ and ring A are as hereinbefore defined, $R^1$ is hydrogen and

----- is a single or a double bond may be prepared by conversion of a compound of formula (II) wherein ring A, and $R^{10}$ are as hereinbefore defined and $R^1$ is hydroxymethyl,

----- by oxidation of the hydroxymethyl group, using for e.g. Swern conditions, to yield a compound of formula (II) wherein $R^1$ is a formyl group.

A compound of formula (II) wherein $R^1$ is a formyl group may subsequently be treated with a Wittig reagent such as the one generated by the action of base on methyltriphenylphosphonium bromide to yield a compound of formula (VII)

-----.

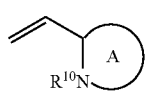
(VIII)

This material may be reacted with an optionally substituted haloaryl or haloheteroaryl compound, wherein the halogen is iodine or bromine, in the presence of a tertiary amine (such as triethyl amine) and a palladium catalyst such as Bis(triphenylphosphine)-palladium(II) chloride. The reaction is generally run at elevated temperature (80-120° C.) in an aprotic solvent such as DMF to obtain a compound of formula (IX).

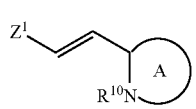
(IX)

Wherein one of the ring substituents of $Z^1$ is cyano, compound (IX) may be treated with $H_2S$, pyridine, TEA; MeI/acetone at room temperature to reflux preferably at 50° C.; $NH_4OAc$/methanol at room temperature to reflux preferably at 60° C. or with HCl/MeOH; $NH_3$/MeOH at room temperature to reflux preferably at 60° C. to give a compound of formula (IX) wherein one of the ring substituents of $Z^1$ is amidino. When the nitrogen protecting group is a t-butyloxycarbonyl or other acid labile protecting group, this group is removed by the action of said reagents, to obtain a compound of formula (X) directly. Otherwise the nitrogen protecting function may be removed as appropriate to obtain (X).

In either case the resulting amine X is subsequently reacted with a compound of formula (VI) as previously described to obtain a compound of formula I wherein $R^1$ is Hydrogen, $Z^1$ is an amidino substituted aryl and A and $R^2$ are as herein before defined.

In the reactions described, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, 1991.

It will be apparent to those skilled in the art that certain compounds of formula I can exhibit isomerism, for example geometrical isomerism, e.g., E or Z isomerism, and optical isomerism, e.g., R or S configurations. Geometrical isomers include the cis and trans forms of compounds of the invention having alkenyl moieties. Individual geometrical isomers and stereoisomers within formula I, and their mixtures, are within the scope of the invention.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

Guidance in the separation of stereoisomeric mixtures can be found, by way of example and not limitation, in "Enantiomers, Racemates, and resolutions", Jean Jacques, Andre Collet, and Samuel H. Wilen (Krieger Publishing Company, Malabar, Fla., 1991, ISBN 0-89464-618-4). In particular, Part 2, "Resolution of Enantiomer Mixture", pages 217-435; more particularly, section 4, "Resolution by Direct Crystallization", pages 217-251, section 5, "Formation and Separation of Diastereomers", pages 251-369, section 6, "Crystallization-Induced Asymmetric Transformations", pages 369-378, and section 7, "Experimental Aspects and Art of Resolutions", pages 378-435; still more particularly, section 5.1.4, "Resolution of Alcohols, Transformation of Alcohols into Salt-Forming Derivatives", pages 263-266, section 5.2.3, "Covalent Derivatives of Alcohols, Thiols, and Phenols", pages 332-335, section 5.1.1, "Resolution of Acids", pages 257-259, section 5.1.2, "Resolution of Bases", pages 259-260, section 5.1.3, "Resolution of Amino Acids", page 261-263, section 5.2.1, "Covalent Derivatives of Acids", page 329, section 5.2.2, "Covalent Derivatives of Amines", pages 330-331, section 5.2.4, "Covalent Derivatives of Aldehydes, Ketones, and Sulfoxides", pages 335-339, and section 5.2.7, "Chromatographic-Behavior of Covalent Diastereomers", pages 348-354, are cited as examples of the skill of the art.

A compound of formula I including an heteroaryl group containing one or more nitrogen ring atoms, preferably imine (=N—), may be converted to the corresponding compound wherein one or more nitrogen ring atom of the heteroaryl moiety is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on Factor Xa inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-B-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution. The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on Factor Xa inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared. The base addition salts of the compounds of this invention can be regenerated from the salts by the application or adaptation of known methods. For example, parent compounds of the invention can be regenerated from their base addition salts by treatment with an acid, e.g. hydrochloric acid.

Pharmaceutically acceptable salts also include quaternary lower alkyl ammonium salts. The quaternary salts are prepared by the exhaustive alkylation of basic nitrogen atoms in compounds, including nonaromatic and aromatic basic nitrogen atoms, according to the invention, i.e., alkylating the non-bonded pair of electrons of the nitrogen moieties with an alkylating agent such as methylhalide, particularly methyl iodide, or dimethyl sulfate. Quaternarization results in the nitrogen moiety becoming positively charged and having a negative counter ion associated therewith.

As will be self-evident to those skilled in the art, some of the compounds of this invention do not form stable salts. However, acid addition salts are more likely to be formed by compounds of this invention having a nitrogen-containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art. The starting materials and intermediates are prepared by the application or adaptation of known methods, for example methods as described in the Reference Examples or their obvious chemical equivalents, or by methods according to this invention.

The present invention is further exemplified but not limited by the following illustrative examples which illustrate the preparation of the compounds according to the invention.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad.

Experimental

EXAMPLE 1

2-[1-(Biphenyl-4-carbonyl)-pyrrolidin-2-yl]-3-(3-carbamimidoylphenyl)-propionic acid methyl ester trifluoroacetate A. (R)-1-(tert-Butyloxycarbonyl)pyrrolidin-2-yl-acetic acid methyl ester (R)-1-(tert-Butyloxycarbonyl)pyrrolidin-2-yl-carboxylic acid (9.7 g, 48 mmol) is dissolved in THF (250 mL) cooled to −30° C. and treated with NMM (5.75 mL, 52 mmol), isobutyl chloroformate (6.79 mL, 52 mmol) and stirred for 20 min. The reaction mixture is filtered and the filtrate is added to a solution of diazomethane (~71 mmol) in ether (200 mL) at 0° C. The reaction mixture is stirred for 20 min. then quenched with acetic acid dropwise. The solvent is removed under vacuo and the residue is dissolved in methanol (100 mL) and treated with a solution of silver benzoate (2.18 g, 9.5 mmol) in triethylamine (21.4 mL) for 35 min. The reaction mixture is concentrated, diluted with ethyl acetate (600 mL) and washed with saturated sodium bicarbonate (3×150 mL), water (3×150 mL), potassium sulfite (3×150 mL) and brine. The organic layer is dried (MgSO$_4$) and concentrated; flash chromatography gives the title compound as a clear oil (5.3 g, 21.8 mmol). $^1$H NMR (CDCl$_3$, 300 MHz) □ 4.1(br.s., 1H), 3.66(s, 3H), 3.38-3.28(m, 2H), 2.92-2.80(m, 1H), 2.30(dd, 1H), 2.10-1.98(m, 1H), 1.90-1.65(m, 3H), 1.43(s, 9H).

B. 2-[1-(Biphenyl-4-carbonyl)-pyrrolidin-2-yl]-3-(3-cyanophenyl)-propionic acid methyl ester (R)-1-(tert-Butyloxycarbonyl)pyrrolidin-2-yl-acetic acid methyl ester (2.0 g, 8.2 mmol) is treated with THF (50 mL) and a 1 M solution of lithium bis(trimethylsilyl)amide in THF (24.7 mL, 24.7 mmol) at −75° C. under nitrogen. The reaction mixture is warmed to −30° C. for 30 min then cooled to −70° C. and treated dropwise with a solution of 3-bromomethylbenzonitrile (4.03 g, 20.7 mmol) in THF (20 mL). The reaction mixture is warmed to room temperature over 2 h then quenched with saturated bicarbonate (100 mL) and concentrated to remove organic solvent. The aqueous mixture is taken up in ethyl acetate (300 mL) and additional saturated bicarbonate solution (150 mL) and separated. The organic layer is washed with bicarbonate and brine, dried over magnesium sulfate and concentrated to give a yellow solid. The solid is extracted with 20% ethyl acetate/hexane; evaporation of the solvent gives 2-[1-(tert-Butyloxycarbonyl)pyrrolidin-2-yl]-3-(3-cyanophenyl)-propionic acid methyl ester as a tan oil. This material is treated with methylene chloride (30 mL) and trifluoroacetic acid (10 mL) at 0° C. for 2 h. The volatiles are removed and the residue is purified by reverse phase HPLC. The 3-(3-cyanophenyl)-2-(pyrrolidin-2-yl)propionic acid methyl ester trifluroacetate so obtained is taken up in 1 N HCl and washed with ethyl ether (3×50 mL). The aqueous solution is basified with sodium bicarbonate (5 g) and extracted with ethyl acetate (3×100 mL). The combined organic layers are dried over magnesium sulfate and evaporated to dryness to give a crude mixture of isomers of 3-(3-Cyanophenyl)-2-(pyrrolidin-2-yl)-propionic acid methyl ester (0.88 g, 3.4 mmol). This material is used in the following reaction without further purification. Biphenyl-4-carboxylic acid (0.67 g, 3.4 mmol) is treated with DMF (15 mL), diisopropylethyl amine (0.59 mL, 3.4 mmol), TBTU (1.43 g, 3.4 mmol) until a homogenous solution is obtained. To this is added 3-(3-Cyanophenyl)-2-(pyrrolidin-2-yl)-propionic acid methyl ester (0.88 g, 3.4 mmol) in DMF (7.5 mL) and the reaction mixture is stirred at 35 C for 16 h. The reaction mixture is diluted with ethyl acetate (300 mL), washed with 1 N HCl (3×50 mL), water (3×50 mL), saturated bicarbonate and brine. The organic layer is dried over MgSO$_4$, and concentrated to a residue which is chromatographed (methylene chloride:hexane:ethyl acetate; 5:4:1) to give the title compound (1.02 g, 2.3 mmol). $^1$H NMR (CDCl$_3$, 300 MHz) □ 7.70-7.30(m, 13H), 4.70, 4.47(two m, 1H), 3.85-3.72(m, 1H), 3.66, 3.62 (two s, 3H), 3.62-3.40(m, 2H), 3.20-3.08(m, 1H), 2.90-2.75 (m, 1H), 2.20-2.05(m, 1H), 2.02-1.60(m, 3H).

C. 2-[1-Biphenyl-4-carbonyl)-pyrrolidin-2-yl]-3-(3-carbamimidoylphenyl)-propionic acid methyl ester trifluoroacetate 2-[1-(Biphenyl-4-carbonyl)-pyrrolidin-2-yl]-3-(3-cyanophenyl)-propionic acid methyl ester (1.02 g, 2.3 mmol) is dissolved in pyridine (19.6 mL) and triethyl amine (4 mL), chilled and saturated with a stream of H$_2$S gas. The reaction vessel is sealed and warmed to ambient temperature for 16 h. The vessel is vented and the contents are concentrated in vacuo. The residue is treated with acetone (20 mL) and methyl iodide (5 mL, excess) and warmed to reflux for 3 o min. The reaction mixture is concentrated to a solid and treated with methanol (30 mL) and ammonium acetate (0.5 g, 6.5 mmol) and heated to 60° C. under nitrogen for 3 hrs. The solvent is removed in vacuo and the residue is subjected to reverse phase HPLC purification (40-90% CH$_3$CN/0.1% aqueous TFA over 30 min) to give the title compound as a white solid (0.71 g, 1.2 mmol). $^1$H NMR (DMSO-d$_6$, 300 MHz) □ 9.45(d, 2H), 9.32(d, 2H), 7.75-7.32 (m, 13H), 4.52, 4.36(two m, 1H), 3.58, 3.51 (two s, 3H), 3.50-3.25(m, 3H), 3.14-2.95(m, 1H), 2.95-2.80(m, 1H), 2.20-1.55(m, 4H). MS m/z: [M+H]$^+$=456. Chiral HPLC analysis indicates this product to be mixturres of four stereoisomers.

EXAMPLE 2

3-(3-Carbamimidoylphenyl)-2-[1-(4-pyridin-3-yl-benzoyl)-pyrrolidin-2-yl]propionic acid methyl ester ditrifluoroacetate A. 3-(3-Cyanophenyl)-2-[1-(4-pyridin-3-ylbenzoyl)-pyrrolidin-2-yl]propionic acid methyl ester 4-Pyridin-3-ylbenzoic acid (0.83 g, 3.5 mmol) and 3-(3-cyanophenyl)-2-(pyrrolidin-2-yl)-propionic acid methyl ester (0.91 g, 3.5 mmol) are coupled as described in EXAMPLE 1B to give the title compound (1.22 g, 2.8 mmol). $^1$H NMR (CDCl$_3$, 300 MHz) □ 8.98(s, 1H), 8.75(d, 1H), 8.58(d, 1H), 8.03(m, 1H), 7.85-7.60(m, 4H), 4.72-4.45 (two m, 1H), 3.80-3.71(m, 1H), 3.68, 3.62(two s, 3H), 3.63-3.40(m, 2H), 3.21-3.10(m, 1H), 2.90-2.78(m, 1H), 2.20-2.05(m, 1H), 2.02-1.50(m, 3H).

B. 3-(3-Carbamimidoylphenyl)-2-[1-(4-pyridin-3-ylbenzoyl)-pyrrolidin-2-yl]propionic acid methyl ester ditrifluoroacetate 3-(3-Cyanophenyl)-2-[1-(4-pyridin-3-ylbenzoyl)-pyrrolidin-2-yl]propionic acid methyl ester (1.22 g, 2.8 mmol) is treated with methylene chloride (25 mL), and a saturated solution of methanolic HCl (75 mL) at 0° C. The reaction vessel is sealed and the solution is warmed to room temperature over 48 h. The volatiles are removed and the residue is treated with a saturated solution of ammonia in methanol at 0° C. The reaction vessel is fitted with a reflux condenser and a balloon and the reaction mixture is warmed to 60° C. for 3 h. The volatiles are removed and the residue is purified by reverse phase HPLC to give the title compound (0.39 g, 0.57 mmol). $^1$H NMR (DMSO-$d_6$, 300 MHz) ☐9.43-9.25(m, 4H), 9.06(s, 1H), 8.72(m, 1H), 8.42(d, 1H), 7.91-7.45(m, 9H), 4.52, 4.34(two m, 1H), 3.60, 3.52(two s, 3H), 3.50-3.25(m, 3H), 3.14-2.95(m, 1H), 2.94-2.80(m, 1H), 2.18-1.55 (m, 4H). MS m/z: [M+H]$^+$=457.

EXAMPLE 3

2-[1-(3-Aminomethylbiphenyl-4-carbonyl)-pyrrolidin-2-yl]-3-(3-carbamimidoylphenyl)-propionic acid methyl ester ditrifluoroacetate

A. 2-{1-[3-(tert-Butyloxycarbonylaminomethyl)biphenyl-4-carbonyl]-pyrrolidin-2-yl}-3-(3-cyanophenyl)-propionic acid methyl ester 3-(tert-Butyloxycarbonylaminomethyl)biphenyl-4-carboxylic acid (1.15 g, 3.5 mmol) and 3-(3-cyanophenyl)-2-(pyrrolidin-2-yl)-propionic acid methyl ester (0.91 g, 3.5 mmol) are coupled as described in EXAMPLE 1B to give the title compound (1.22 g, 2.8 mmol). $^1$H NMR (CDCl$_3$, 300 MHz) ☐ 7.63-7.25(m, 12H), 4.85-4.70(two m, 1H), 4.48(m, 1H), 4.38(br.s, 2H), 3.80-3.71(m, 1H), 3.68, 3.62 (two s, 3H), 3.63-3.40(m, 2H), 3.21-3.10(m, 1H), 2.90-2.78 (m, 1H), 2.20-2.05(m, 1H), 2.02-1.65(m, 3H), 1.45(s, 9H).

B. 2-[1-(3-Aminomethylbiphenyl-4-carbonyl)-pyrrolidin-2-yl]-3-(3-carbamimidoylphenyl)-propionic acid methyl ester ditrifluoroacetate 2-{1-[3-(tert-Butyloxycarbonylaminomethyl)biphenyl-4-carbonyl]-pyrrolidin-2-yl}-3-(3cyanophenyl)-propionic acid methyl ester (1.75 g, 3.1 mmol) is treated as described in EXAMPLE 1C to obtain crude 2-{1-[3-(tert-Butyloxycarbonylaminomethyl)biphenyl-4-carbonyl]-pyrrolidin-2-yl}-3-(3-carbamimidophenyl)-propionic acid methyl ester which is used without further purification. This material is stirred in methylene chloride (30 mL) at 0° C. and treated with trifluoroacetic acid (5 mL). The reaction is warmed to RT and stirred 2 h. The reaction mixture is concentrated and the residue is purified by HPLC (40-90% CH$_3$CN/0.1% aqueous TFA over 30 min) to give the title compound (1.31 g, 1.8 mmol). NMR (DMSO-$d_6$, 300 MHz) ☐9.25(m, 4H), 8.29(s, 3H), 7.85-7.42(m, 12H), 4.52, 4.34(two m, 1H), 4.11 (d, 2H), 3.60, 3.52(two s, 3H), 3.50-3.25(m, 3H), 3.14-2.95 (m, 1H), 2.94-2.80(m, 1H), 2.18-1.55(m, 4H). MS m/z: [M+H]$^+$=485.

EXAMPLE 4

3-(3-Carbamimidoylphenyl)-2-[1-(6-chlorobenzo[b]thiophene-2-carbonyl)-pyrrolidin-2-yl]-propionic acid methyl ester trifluoroacetate 6-Chlorobenzo[b]thiophene-2-carboxylic acid (0.24 g, 1.14 mmol) is coupled to 3-(3-cyanophenyl)-2-(pyrrolidin-2-yl)-propionic acid methyl ester (0.295 g, 1.14 mmol) as described in EXAMPLE 1B to give 3-(3-cyanophenyl)-2-[1-(6-chlorobenzo[b]thiophene-2-carbonyl)-pyrrolidin-2-yl]-propionic acid methyl ester (0.40 g, 0.89 mmol). This material is treated and purified as described in EXAMPLE 1C to obtain the title compound (0.27 g, 0.46 mmol). NMR (DMSO-$d_6$, 300 MHz) ☐9.31-9.15(m, 4H), 8.13(s, 1H), 7.95-7.85(m, 2H), 7.62-7.40(m, 5H), 4.53, 4.38(two m, 1H), 3.95-3.55(m, 2H), 3.60-3.53(m, 1H), 3.52-3.49(two s, 3H), 3.14-2.95(m, 1H), 2.94-2.80(m, 1H), 2.18-1.55(m, 4H): MS m/z: [M+H]$^+$=470. Elemental analysis calculated with 1.0 mole of H$_2$O: C=51.87, H=4.52, N=6.98; found C=51.93, H=4.23, N=6.75.

EXAMPLE 5

3-(3-Carbamimidoylphenyl)-2-{1-[4-(6-methoxypyrid-3-yl)-benzoyl]-pyrrolidin-2-yl}-propionic acid methyl ester ditrifluoroacetate

A. 3-(3-Cyanophenyl)-2-{1-[4-(6-methoxypyrid-3-yl)benzoyl]-pyrrolidin-2-yl}-propionic acid methyl ester 1-(6-methoxypyrid-3-yl)benzoic acid (0.30 g, 1.3 mmol) is coupled to 3-(3-cyanophenyl)-2-(pyrrolidin-2-yl)-propionic acid methyl ester (0.34 g, 1.3 mmol) as described in EXAMPLE 1B to give the title compound (0.40 g, 0.85 mmol). $^1$H NMR (CDCl$_3$, 300 MHz) ☐ 8.38(s, 1H), 7.80(d, 1H), 7.62-7.28(m, 8H), 6.83(d, 1H), 4.71, 4.47(two m, 1H), 3.96(s, 3H), 3.82-3.72(m, 1H), 3.66, 3.62(two s, 3H), 3.60-3.41(m, 2H), 3.20-3.08(m, 1H), 2.90-2.75(m, 1H), 2.20-2.06 (m, 2H), 2.00-1.55(m, 2H).

B. 3-(3-Carbamimidoylphenyl)-2-{1-[4-(6-methoxypyrid-3-yl)-benzoyl]-pyrrolidin-2-yl}-propionic acid methyl ester ditrifluoroacetate 3-(3-Cyanophenyl)-2-{1-[4-(6-methoxypyrid-3-yl)benzoyl]-pyrrolidin-2-yl}-propionic acid methyl ester (0.075 g, 0.16 mmol) is treated and purified as described in EXAMPLE 2B to obtain the title compound (0.042 g, 0.07 mmol). $^1$H NMR (DMSO-$d_6$, 300 MHz) ☐ 9.28(d, 2H), 9.08(d, 2H), 8.52(s, 1H), 8.04(dd, 1H), 7.78-7.45(m, 8H), 6.93(d, 1H), 4.52, 4.36(two m, 1H), 3.96(s,3H), 3.58, 3.51 (two s, 3H), 3.50-3.25(m,3H), 3.14-2.95(m, 1H), 2.95-2.80 (m, 1H), 2.20-1.55(m, 4H). MS m/z: [M+H]$^+$=487. Elemental analysis calculated with 1.0 mole of H$_2$O: C=52.46, H=4.68, N=7.65; found C=52.46, H=4.54, N=7.54.

EXAMPLE 6

3-(3-Carbamimidoylphenyl)2-{1-[4-(6-oxo-1,6-dihydropyrid-3-yl)benzoyl]-pyrrolidin-2-yl}-propionic acid methyl ester trifluoroacetate 3-(3-Cyanophenyl)-2-{1-[4-(6-methoxypyrid-3-yl)benzoyl]-pyrrolidin-2-yl}-propionic acid methyl ester (0.33 g, 0.70 mmol) is treated with pyridine hydrochloride (1.32 g, 8.44 mmol) and heated to 160° C. for 10 min. The reaction mixture is cooled and mixed with water (15 mL); the aqueous solution is decanted. The residual solid is partitioned between methylene chloride (25 mL) and saturated bicarbonate and separated. The organic layer is washed with bicarbonate (2×10 mL), water, dried (sodium sulfate) and concentrated. The residue, used without further purification, is treated as described in EXAMPLE 2B. HPLC purification gives the title compound (0.032 g, 0.055 mmol). $^1$H NMR (DMSO-$d_6$, 300 MHz) □ 9.26(d, 2H), 8.92(d, 2H), 7.86(dd, 1H), 7.76(s, 1H), 7.71-7.42(m, 8H), 6.43(d, 1H), 4.52, 4.36(two m, 1H), 3.58, 3.51 (two s, 3H), 3.50-3.25(m,3H), 3.14-2.95(m, 1H), 2.95-2.80(m, 1H), 2.20-1.55(m, 4H). MS m/z: [M+H]$^+$=473.

EXAMPLE 7

2-[1-Biphenyl4-carbonyl)-pyrrolidin-2-yl]-3-(3-carbamimidoylphenyl)-propionic acid methyl ester trifluoroacetate (S)-1-(tert-Butyloxycarbonyl)pyrrolidin-2-yl-acetic acid methyl ester (2.0 g, 8.2 mmol) prepared from (S)-1-(tert-Butyloxycarbonyl)pyrrolidin-2-yl-carboxylic acid as described for its enantiomer in EXAMPLE 1A is treated as described in EXAMPLE 1B to obtain 3-(3-cyanophenyl)-2-(pyrrolidin-2-yl)-propionic acid methyl ester (1.07 g, 4.1 mmol) as a mixture of stereoisomers. This material is coupled with biphenyl-4-carboxylic acid to give 2-[1-(Biphenyl-4-carbonyl)-pyrrolidin-2-yl]-3-(3-cyanophenyl)-propionic acid methyl ester (1.0 g, 2.3 mmol). This propionic acid methyl ester compound is then converted to the title compound (0.88 g, 1.5 mmol) by the procedure described in EXAMPLE 1C, which is indistinguishable from the product of EXAMPLE 1 by $^1$H-NMR, mass spec and chiral HPLC.

EXAMPLE 8

2-[1-Biphenyl-4-carbonyl)-pyrrolidin-2-yl]-3-(4-carbamimidoylphenyl)-propionic acid methyl ester trifluoroacetate (R)-1-(tert-Butyloxycarbonyl)pyrrolidin-2-yl-acetic acid methyl ester (0.5 g, 2.06 mmol) is treated with lithium bis(trimethylsilyl)amide and 4-bromomethylbenzonitrile (1.0 g, 5.14 mmol) as described in EXAMPLE 1B to give 3-(4-cyanophenyl)-2-(pyrrolidin-2-yl)-propionic acid methyl ester as a mixture of stereoisomers. This material is coupled with biphenyl-4-carboxylic acid to give 2-[1-(Biphenyl-4-carbonyl)-pyrrolidin-2-yl]-3-(4-cyanophenyl)-propionic acid methyl ester (0.5 g, 1.1 mmol). This material is converted to the title compound (0.47 g, 0.83 mmol) by the procedure described in EXAMPLE 1C. $^1$H NMR (DMSO-$d_6$, 300 MHz) □ 9.35-9.11(m,4H), 7.78-7.32 (m, 13H), 4.52, 4.36(two m, 1H), 3.58, 3.51 (two s, 3H), 3.50-3.25(m,3H), 3.14-2.95(m, 1H), 2.95-2.80(m, 1H), 2.20-1.55(m, 4H). MS m/z: [M+H]$^+$=456

EXAMPLE 9

2-[1-(Biphenyl-4-carbonyl)-pyrrolidin-2-yl]-3-(1H-pyrrolo[3,2-c]pyridin-2-yl)-propionic acid methyl ester trifluoroacetate A. (R)-1-(Biphenyl-4-carbonyl)-pyrrolidin-2-yl]-acetic acid methyl ester A flask containing (R)-1-(tert-Butyloxycarbonyl)pyrrolidin-2-yl-acetic acid methyl ester (2.5 g, 10.3 mmol) and dry MeOH (35 mL) is stirred at 0° C. HCl gas is bubbled through the solution for 5 minutes and the reaction is warmed to RT. The mixture is concentrated to give (R)-pyrrolidin-2-yl-acetic acid methyl ester hydrochloride as a white solid (1.85 g, 10.3 mmol) which is used directly in the next step. 4-Biphenyl carboxylic acid (2.04 g, 10.3 mmol) and DMF (10 mL) is treated with diisopropylethylamine (5.37 mL, 30.9 mmol) and TBTU (3.30 g, 10.3 mmol) with stirring. After 2 minutes (R)-pyrrolidin-2-yl-acetic acid methyl ester hydrochloride (1.85 g, 10.3 mmol) is added and the reaction stirred ~16 h at 35° C. The reaction is diluted with EtOAc (200 mL) and washed with 1 N HCl (3×50 mL), water, saturated sodium bicarbonate (3×50 mL), brine, dried over MgSO$_4$ and concentrated. Purification by flash chromatography (35% to 50% EtOAc/hexanes) gives the title compound as a white solid (3.34 g, 5.57 mmol). $^1$H NMR (CDCl$_3$, 300 MHz) □ 7.65-7.52(m, 6H), 7.50-7.31(m, 3H), 4.54(m, 1H), 3.68(s, 3H), 3.65-3.45(m, 2H), 3.08(dd, 1H), 2.66(dd, 1H), 2.28(m, 1H), 1.95-1.71(m, 3H).

B. 2-[1-(Biphenyl-4-carbonyl)-pyrrolidin-2-yl]-pent-4-ynoic acid methyl ester

A flask containing (R)-1-(Biphenyl-4-carbonyl)-pyrrolidin-2-yl]-acetic acid methyl ester (2.35 g, 7.27 mmol) and THF (150 mL) is stirred at −78° C. under nitrogen. A 1M solution of LHMDS in THF (14.9 ml, 14.9 mmol) is added dropwise and the mixture warmed to −30° C. over 30 minutes. The reaction is stirred an additional 30 minutes at −30° C. and cooled to −70° C. A solution of propargyl bromide (2.8 g, 9.45 mmol) in THF (10 mL) is added dropwise and the reaction is warmed to −15° C. The reaction is stirred at −15° C. for 30 minutes and then stirred an additional 30 minutes at −5° C. The reaction is quenched with saturated sodium bicarbonate (15 mL) and partially evaporated to a volume of 20 mL which is partitioned between EtOAc (300 mL) and saturated sodium bicarbonate (150 mL). The organic phase is washed with saturated sodium bicarbonate (2×150 mL), brine, dried over MgSO$_4$ and concentrated to give the crude product. Purification by flash chromatography (4.5:4.5:0.5/CH$_2$Cl$_2$:hexanes:EtOAc) gives the title compound as an amber oil (1.22 g, 3.38 mmol). $^1$H NMR (CDCl$_3$, 300 MHz) □7.68-7.55(m, 6H), 7.50-7.31(m, 3H), 4.81-4.62(m, 1H), 3.76, 3.72(two s, 3H), 3.62-3.38(m, 3H), 2.75-2.61(m, 1H), 2.50(dd, 1H), 2.15-1.61(m, 5H).

C 2-{2-[1-(Biphenyl-4-carbonyl)-pyrrolidin-2-yl]-2-methoxycarbonyl)-ethyl}-pyrrolo[3,2-c]pyridine-1-carboxylic acid tert-butyl ester A flask is charged with 2-[1-(Biphenyl-4-carbonyl)-pyrrolidin-2-yl]-pent-4-ynoic acid methyl ester (0.58 g, 1.62 mmol), (3-iodopyridin-4-yl)-carbamic acid tert-butyl ester (0.52 g, 1.62 mmol), bis(triphenylphosphine)-palladium(II) chloride (0.057 g, 0.081 mmol), copper iodide (0.0104 g, 0.055 mmol), triethylamine (0.90 mL, 6.5 mmol) and DMF (7.3 mL) and heated at 90° C. for 2 h. The reaction is cooled to RT and partitioned between EtOAc (200 mL) and saturated sodium bicarbonate (75 mL). The organic layer is washed with saturated sodium bicarbonate (2×75 mL), brine (50 mL), dried over MgSO$_4$ and concentrated. The residue is subjected to flash chromatography (1:1/EtOAc:hexanes) to give 2-[1-(biphenyl-4-carbonyl)-pyrrolidin-2-yl]-5-(4-tert-butoxycarbonylamino-pyridin-3-yl)-pent-4-ynoic acid methyl ester as an impure mixture (0.35 g, three components) which is used without further purification. This material (0.35 g, 0.63 mmol estimated), DBU (0.19 g, 1.26 mmol) and acetonitrile (7 mL) is stirred at 50° C. for 6 h. The reaction mixture is concentrated and purified by flash chromatography (0.5% MeOH/CH$_2$Cl$_2$) to (2.0% MeOH/CH$_2$Cl$_2$) to give the title compound (0.18 g, 0.325 mmol). $^1$H NMR (CDCl$_3$, 300 MHz) □8.83(s, 1H), 8.41(m, 1H), 8.25(d, 1H), 7.65-7.53(m, 6H), 7.52-7.32(m, 3H), 6.80(s, 1H), 4.84-4.68(m, 1H), 3.73, 3.68(two s, 3H), 3.67-3.35(m, 6H), 2.21-1.91(m, 4H), 1.67(s, 9H).

D. 2-[1-(Biphenyl-4-carbonyl)-D-pyrrolidin-2-yl]-3-(1H-pyrrolo[3,2-c]pyridin-2-yl)-propionic acid methyl ester-trifluoroacetate A flask containing 2-{2-[1-(Biphenyl-4-carbonyl)-pyrrolidin-2-yl]-2-methoxycarbonyl)-ethyl}-pyrrolo[3,2-c]pyridine-1-carboxylic acid tert-butyl ester (0.18 g, 0.325 mmol) and CH$_2$Cl$_2$ (15 mL) is stirred at 0° C. To this is added TFA (5 mL), the reaction is warmed to RT and stirred an additional 3 h. The volatiles are evaporated and the residue is purified by reverse phase HPLC (gradient elution of 30% acetonitrile/water(0.1% TFA) to 100% acetonitrile) and lyophilized to give the title compound as a white solid (0.105 g, 0.185 mmol). $^1$H NMR (DMSO-d$_6$, 300 MHz) □ 12.85(s, 2H), 9.08(s, 1H), 8.31(d, 1H), 7.82(d, 1H), 7.70-7.55(m, 4H), 7.50-7.32(m, 5H), 6.74(s, 1H), 4.58(m, 1H), 3.65, 3.61 (two s, 3H), 3.55-3.03(m, 5H), 2.08-1.61 (m, 4H). MS m/z: [M+H]$^+$=454.

EXAMPLE 10

2-[1-(Biphenyl-4-carbonyl)-D-pyrrolidin-2-yl]-3-(1H-pyrrolo[2,3-c]pyridin-2-yl)-propionic acid methyl ester-trifluoroacetate The title compound is prepared as in EXAMPLE 9, using 4-iodo-pyridin-3-yl-carbamic acid tert-butyl ester in lieu of 3-iodo-pyridin-4-yl-carbamic acid tert-butyl ester in step D. The remainder of the preparation is essentially the same giving the title compound as a white solid (0.092 g, 0.162 mmol). $^1$H NMR (DMSO-d$_6$, 300 MHz) □ 13.02(s, 2H), 8.95(s, 1H), 8.18(d, 1H), 7.95(d, 1H), 7.75-7.55(m, 4H), 7.53-7.30(m, 5H), 6.70(s, 1H), 4.58(m, 1H), 3.65, 3.61(two s, 3H), 3.45-3.10(m, 5H), 2.21-1.60(m, 4H). MS m/z: [M+H]$^+$=454.

EXAMPLE 11

3-(4-Amino-quinazolin-6-yl)-2-[1-(biphenyl-4-carbonyl)-D-pyrrolidin-2-yl]-propionic acid methyl ester-ditrifluoroacetate

A. 6-Bromomethyl-4-chloro-quinazoline

A flask containing 4-Chloro-6-methylquinazoline (0.91 g, 5.09 mmol), NBS (0.95 g, 5.35 mmol), benzoyl peroxide 70% (0.09 g, 0.2545 mmol) and carbon tetrachloride (25 mL) is refluxed at 80° C. for 20 h. The solution is cooled to RT, filtered and concentrated. Purification by flash chromatography (7.5% EtOAc/hexanes) yields the title compound as a white solid (0.62 g, 2.42 mmol). $^1$H NMR (CDCl$_3$, 300 MHz) □9.06(s, 1H), 8.25(s, 1H), 8.07(d, 1H), 8.00(d, 1H), 4.67(s, 2H).

B. 2-[1-(Biphenyl-4-carbonyl)-pyrrolidin-2-yl]-3-(4-chloro-quinazolin-6-yl)-propionic acid methyl ester A flask containing (R)-1-(Biphenyl-4-carbonyl)-pyrrolidin-2-yl]-acetic acid methyl ester (0.14 g, 1.43 mmol) and THF (20 mL) is stirred at −78° C. under nitrogen. A 1 M solution of LHMDS in THF (1.58 ml, 1.58 mmol) is added dropwise and the mixture is warmed to −30° C. over 30 minutes. The reaction is stirred an additional 30 minutes at −30 ° C., then cooled to −70° C. A solution of 6-Bromomethyl-4-chloro-quinazoline (0.55 g, 2.15 mmol) in THF (10 mL) is added dropwise and the reaction is warmed to RT over 1 h. The reaction is stirred at RT for 3 h. The reaction is quenched with saturated sodium bicarbonate (50 mL) and partially evaporated to a volume of 20 mL. This mixture is partitioned between EtOAc (300 mL) and saturated sodium bicarbonate solution (150 mL). The organic phase is washed with saturated sodium bicarbonate (2×150 mL), brine, dried over MgSO$_4$ and concentrated to give crude residue. Purification by flash chromatography (35% EtOAc/hexanes) gives the title compound as an amber oil (0.28 g, 0.56 mmol). $^1$H NMR (CDCl$_3$, 300 MHz) □8.97(s, 1H), 8.12(s, 1H), 7.96(d, 1H), 7.84(d, 1H), 7.64-7.53(m, 6H), 7.48-7.33 (m, 3H), 4.80(m, 1H), 3.91-3.75(m, 1H), 3.66(s, 3H), 3.62-3.50(m, 2H), 3.46-3.32(m, 1H), 3.10-3.00(m, 1H), 2.20-2.10 (m, 1H), 2.06-1.93(m, 2H), 1.90-1.72(m, 1H).

C. 3-(4-Amino-quinazolin-6-yl)-2-[1-(biphenyl-4-carbonyl)-D-pyrrolidin-2-yl]-propionic acid methyl ester-ditrifluoroacetate A flask containing 2-[1-(Biphenyl-4-carbonyl)-pyrrolidin-2-yl]-3-(4-chloro-quinazolin-6-yl)-propionic acid methyl ester (0.16 g, 0.32 mmol) and anhydrous 2-propanol (20 mL) is stirred under nitrogen at 0° C. Ammonia gas is bubbled through the solution for 10 minutes. Acetic acid (2 drops) is added and the mixture stirred at 50° C. for 4 h. The reaction is concentrated and purified by reverse phase HPLC (gradient elution of 30% to 90% acetonitrile/0.1% aqueous TFA) and lyopholized to give the title compound as a white solid (0.16 g, 0.226 mmol). $^1$H NMR (DMSO-d$_6$, 300 MHz) □9.80-9.60(m, 2H), 8.74(s, 1H), 8.28(s, 1H), 7.85(d, 1H), 7.77-7.60(m, 5H), 7.54-7.31(m, 5H), 4.60-4.48(m, 1H), 3.70-3.61(m, 1H), 3.55-3.52(two s, 3H), 3.25-2.95(m, 4H), 2.10-1.60(m, 4H). MS m/z: [M+H]$^+$=481.

EXAMPLE 12

3-(R)-(3-Carbamimidoylphenyl)-2-(R)-{1-[4-(6-oxo-16-dihydropyrid-3-yl)-benzoyl]-pyrrolidin-2-yl}-propionic acid methyl ester trifluoroacetate

A. 3-(R)-(3-Cyanophenyl)-2-(R)-(pyrrolidin-2-yl}-propionic acid methyl ester (R)-1-(tert-Butyloxycarbonyl)pyrrolidin-2-yl-acetic acid methyl ester (5.0 g, 20.6 mmol), prepared as described in EXAMPLE 1A, is treated with ethyl acetate saturated with HCl gas to give (R)-pyrrolidin-2-yl-acetic acid methyl ester hydrochloride as a white solid (3.62 g, 20.3 mmol) which is used directly in the next step. This material (4.69 g, 26.3 mmol) is treated with THF (85 mL) and a 1 M solution of lithium bis(trimethylsilyl)amide in THF (52.5 mL, 52.5 mmol) at −15° C. under nitrogen. After stirring 10 min at −15° C. a solution of 3-bromomethyl-benzonitrile (4.63 g, 23.8 mmol) in THF (30 mL) is added dropwise. The reaction mixture is stirred at −15° C. for an additional 30 min and then warmed to −5° C. for 30 min. The reaction is quenched with methanol and concentrated to dryness. The residue is taken up in methylene chloride and extracted with saturated bicarbonate (250 mL). The aqueous layer is washed with methylene chloride (2×); the organic layers are combined and washed with water, dried over sodium sulfate and concentrated to give the title compound as an amber oil (5.82 g, 22 mmol).
$^1$H NMR (CDCl$_3$, 300 MHz) ☐ 7.56-7.32(m, 4H), 3.91-3.65(m, 1H), 3.61 (s, 3H), 3.58-3.45(m, 1H), 3.72-2.90(m, 4H), 2.15-1.78(m, 3H), 1.72-1.55(m, 1H).

B. (R)-3-(3-Cyanophenyl)-2-{1-[4-(6-methoxypyrid-3-yl)benzoyl]-pyrrolidin-2-yl}-propionic acid methyl ester 1-(6-methoxypyrid-3-yl)benzoic acid (5.05 g, 22 mmol) is treated with DMF (30 mL), diisopropylethyl amine (3.84 mL, 22 mmol), TBTU (7.08 g, 22 mmol) until a homogenous solution is obtained. To this is added 3-(R)-(3-Cyanophenyl)-2-(R)-(pyrrolidin-2-yl}-propionic acid methyl ester (5.82 g, 22 mmol) in DMF (15 mL) and the reaction mixture is stirred at 35° C. for 16 h. The reaction mixture is diluted with ethyl acetate (600 mL), washed with saturated bicarbonate (3×300 mL), brine (100 mL) and dried over MgSO$_4$. The organic layer is concentrated to a brown residue which is chromatographed (50-75% ethyl acetate/hexane) to give the title compound as a white solid (8.03 g, 17.7 mmol). $^1$H NMR (CDCl$_3$, 300 MHz) ☐ 8.42(s, 1H), 7.80(d, 1H), 7.64-7.38(m, 7), 7.36-7.30(m, 1H), 6.83(d, 1H), 4.72(d, 1H), 3.96(s, 3H), 3.63(s, 3H), 3.62-3.42(m, 3H), 3.22-3.07(m, 1H), 2.86-2.73(m, 1H), 2.18-1.68(m, 4H).

C. 3-(R)-(3-Cyanophenyl)-2-(R)-{1-[4-(6-oxo-1,6-dihydropyrid-3-yl)benzoyl]-pyrrolidin-2-yl}-propionic acid methyl ester 3-(R)-(3-Cyanophenyl)-2-(R)-{1-[4-(6-methoxypyrid-3-yl)benzoyl]-pyrrolidin-2-yl-propionic acid methyl ester (8.3 g, 17.7 mmol) is treated with pyridine hydrochloride (13.8 g, 88.4 mmol) and heated to 160° C. for 10 min. The reaction mixture is partitioned between methylene chloride (~300 mL total) and water (100 mL). The organic layer is washed with water, dried (sodium sulfate) and concentrated. The residue obtained is chromatographed (3-6% methanol/methylene chloride) to give the title compound as a white foam (8.0 g, 17.6 mmol). $^1$H NMR (CDCl$_3$, 300 MHz) ☐ 8.08-7.92(m, 2H), 7.66-7.57(m, 3H), 7.54-7.40(m, 4H), 7.39-7.28 (m, 1H), 6.98(d, 1H), 4.78-4.62(m, 1H), 3.63(s, 3H), 3.61-3.40(m, 3H), 3.21-3.05(m, 1H), 2.85-2.73(m, 1H), 2.18-2.04 (m, 1H), 2.02-1.87(m, 2H), 1.86-1.65(m, 1H).

D. 3-(R)-(3-Carbamimidoylphenyl)-2-(R)-{1-[4-(6-oxo-16-dihydropyrid-3-yl)-benzoyl]-pyrrolidin-2-yl}-propionic acid methyl ester trifluoroacetate 3-(R)-(3-Cyanophenyl)-2-(R)-{1-[4-(6-oxo-1,6-dihydropyrid-3-yl)benzoyl]-pyrrolidin-2-yl}-propionic acid methyl ester (8.0 g, 17.6 mmol) is dissolved in pyridine (59 mL) and triethyl amine (12 mL), chilled and saturated with a stream of H$_2$S gas. The reaction vessel is sealed and warmed to ambient temperature for 16 h. The vessel is vented and the contents are concentrated in vacuo. The residue is taken up in THF (100 mL) and methylene chloride (800 mL), washed with 1 N HCl (4×150 mL), water and brine. The organic layer is dried over sodium sulfate and concentrated to dryness. The solid residue is dissolved in warm acetone (220 mL), treated with methyl iodide (20 mL, excess) and warmed to 50° C. for 1 h. The reaction is concentrated, treated with methanol (125 mL) and ammonium acetate (4.07 g, 52.7 mmol) and heated to 60° C. for 3 h. The solvent is removed in vacuo and the residue is purified by HPLC (gradient elution of 20% to 80% acetonitrile/0.1% aqueous TFA) and lyopholized to give the title compound as a white solid (6.0 g, 1.23 mmol). $^1$H NMR (DMSO-d$_6$, 300 MHz) ☐9.26(s, 2H), 9.13(s; 2H), 7.83(d, 1H), 7.78(m, 1H), 7.65-7.56(m, 4H), 7.53-7.41(m, 4H), 6.43(d, 1H), 4.56-4.43(m, 1H), 3.50(s, 3H), 3.49-3.26(m, 3H), 3.12-2.96(m, 1H), 2.91-2.75(m, 1H), 2.04-1.76(m, 3H), 1.75-1.58(m, 1H). MS m/z: [M+H]$^+$=473.

E. 3-(R)-(3-Carbamimidoylphenyl)-2-(R)-{1-[4-(6-oxo-16-dihydropyrid-3-yl)-benzoyl]-pyrrolidin-2-yl}-propionic acid methyl ester A flask containing MP-carbonate (Argonaut Technologies),(0.78 g, 2.45 mmmol) and CH$_2$Cl$_2$ (5 mL) is gently stirred for 5 minutes. The CH$_2$Cl$_2$ is removed by pipette and a solution of 3-(R)-(3-Carbamimidoylphenyl)-2-(R)-{1-[4-(6-oxo-16-dihydropyrid-3-yl)-benzoyl]-pyrrolidin-2-yl}-propionic acid methyl ester trifluoroacetate (0.29 g, 0.49 mmol) in anhydrous MeOH (12 mL) is added and gently stirred for 5 h. The reaction mixture is filtered and the resin washed with CH$_2$Cl$_2$ (4×5 mL). The organic filtrates are combined and concentrated to give the title compound as a white solid (0.21 g, 0.44 mmol). $^1$H NMR (DMSO-d$_6$, 300 MHz) ☐7.86(d, 1H), 7.75(s, 1H), 7.65-7.40(m, 7H), 7.39-7.22(m, 1H), 6.43(d, 1H), 4.56-4.43(m, 1H), 3.48(s, 3H), 3.40-3.15(m, 3H), 3.10-2.92(m, 1H), 2.90-2.75(m, 1H), 2.05-1.80(m, 3H), 1.77-1.58(m, 1H). MS m/z: [M+H]$^+$=473. Elemental analysis calculated with 1.0 mole of H$_2$O: C=66.11, H=6.16, N=11.42; found C=66.03, H=5.88, N=11.19. Chiral HPLC analysis indicates the presence of one stereoisomer.

EXAMPLE 13

3-(R)-(5-Carbamimidoyl-2-hydroxyphenyl)-2-(R)-{1-[4-(6-oxo-1,6-dihydropyrid-3-yl)-benzoyl]-pyrrolidin-2-yl}-propionic acid methyl ester trifluoroacetate

A. 2-(R)-{2-[5-Iodo-2-(2-methoxyethoxy)phenyl]-1-(R)-methyoxycarbonylethyl}pyrrolidine-1-carboxylic acid tert-butyl ester (R)-Pyrrolidin-2-yl-acetic acid methyl ester hydrochloride (0.78 g, 4.4 mmol) is alkylated with 5-Iodo-2-(2-methoxyethoxymethoxy)benzyl bromide (1.5 g, 3.7 mmol) as described in EXAMPLE 12B to yield 3-[5-Iodo-2-(2-methoxyethoxymethoxy)phenyl]-2-pyrrolidin-2-yl propionic acid methyl ester. This material is treated with triethylamine (0.52 mL, 3.74 mmol) and Boc anhydride (0.82 g, 3.74 mmol) in methylene chloride (25 mL) at 0° C. The reaction mixture is warmed to ambient temperature over 3 h. The solvent is removed under vacuo and the residue is partitioned between ethyl acetate and bicarbonate solution. The organic layer is separated, washed with water and brine, dried over MgSO$_4$ and concentrated to a tan oil. This material is chromatographed (25% ethyl acetate/hexane) to give the title compound as an oil (1.66 g, 3.6 mmol). $^1$H NMR (CDCl$_3$, 300 MHz) ☐ 7.43-7.38(m, 2H), 6.88(d, 1H), 5.23(s, 2H), 4.23-4.06(m, 1H), 3.83-3.76(m, 2H), 3.57(s, 3H), 3.56-3.48(m, 2H), 3.37(s, 3H), 3.36-3.26(m, 3H), 2.94-

2.78(m, 1H), 2.76-2.61(m, 1H), 2.03-1.75(m, 4H), 1.45(s, 9H).

B. 2-(R)-{2-[5-Cyano-2-(2-methoxyethoxy)phenyl]-1-(R)-methyoxycarbonylethyl}pyrrolidine-1-carboxylic acid tert-butyl ester 2-(R)-{2-[5-Iodo-2-(2-methoxyethoxy)phenyl]-1-(R)-methyoxycarbonylethyl}pyrrolidine-1-carboxylic acid tert-butyl ester (0.25 g, 0.44 mmol) is dissolved in DMF (5 mL), degassed, and treated with tetrakis(triphenylphosphine) palladium zero (0.05 g, 0.044 mmol) and zinc cyanide (0.156 g, 1.33 mmol) under nitrogen. The reaction mixture is warmed to 73° C. for 2.5 h, cooled and diluted with ethyl acetate (100 mL). The resulting precipitate is removed and the filtrate is washed with water and brine and dried over $MgSO_4$. The solvent is removed in vacuo and the residue is subjected to flash chromatography (ethyl acetate/hexane/methylene chloride: 1/2/1). The title compound is isolated a syrup (0.15 g, mmol). $^1$H NMR ($CDCl_3$, 300 MHz) □ 7.50-7.38(m, 2H), 7.15(d, 1H), 5.31(s, 2H), 4.23-4.11(m, 1H), 3.83-3.76(m, 2H), 3.57(s, 3H), 3.56-3.48(m, 2H), 3.37 (s, 3H), 3.36-3.26(m, 3H), 2.94-2.78(m, 1H), 2.76-2.61(m, 1H), 2.03-1.75(m, 4H), 1.45(s, 9H).

C. 3-(R)-[5-Cyano-2-(2-methoxyethoxyphenyl]-2-(R)-{1-[4-(6-oxo-1,6-dihydropyridin-3-yl)benzoyl]pyrrolidin-2-yl}propionic acid methyl ester 2-(R)-{2-[5-Cyano-2-(2-methoxyethoxy)phenyl]-1-(R)-methyoxycarbonylethyl}pyrrolidine-1-carboxylic acid tert-butyl ester (0.98 g, 2.12 mmol) is treated with methylene chloride (15 mL) and trifluoroacetic acid (5 mL) at 0° C. for 2 h. The volatiles are removed in vacuo and the residue is partitioned between ethyl acetate and saturated bicarbonate solution (100 mL). The organic layer is separated, washed with brine, dried ($MgSO_4$) and evaporated to dryness. The residue is chromatographed (4% methanol/methylene chloride to triethylamine/methanol/methylene chloride:1/5/95) to yield 3-(R)-[5-Cyano-2-(2-methoxyethoxy)phenyl]-2-(R)-pyrrolidin-2ylpropionic acid acid methyl ester (0.43 g, 1.19 mmol). A portion of this material (0.23 g, 0.64 mmol) is coupled with 4-(6-Oxo-1,6-dihydro-pyridin-3-yl)-benzoic acid (0.143 g, 0.64 mmol) as described in EXAMPLE 12, Part C to give the title compound (0.16 g, 0.28 mmol). $^1$H NMR ($CDCl_3$, 500 MHz) □8.32-8.18(m, 2H), 7.75-7.63(m, 2H), 7.62-7.60(m, 1H), 7.58-7.53(m, 2H), 7.50-7.43(m, 1H), 7.35-7.28(m, 1H), 7.14(d, 1H), 5.15, 5.06(two m, 2H), 4.75-4.64(m, 1H), 3.78-3.51(m, 7H), 3.43-3.32(m, 3H), 3.28 (s, 3H), 3.04-2.85(m, 2H), 2.15-2.05(m, 1H), 2.04-1.91(m, 2H), 1.83-1.70(m, 1H).

D. 3-(R)-[5-Carbamimidoyl-2-hydroxyphenyl]-2-(R)-1-[4-(6-oxo-1,6-dihydropyridin-3-yl)benzoyl]-pyrrolidin-2-ylpropionic acid methyl ester trifluoroacetate 3-(R)-[5-Cyano-2-(2-methoxyethoxy)phenyl]-2-(R)-{1-[4-(6-oxo-1,6-dihydropyridin-3-yl)benzoyl]pyrrolidin-2-yl}propionic acid methyl ester (0.16 g, mmol) is treated as described in EXAMPLE 12D to give 3-(R)-[5-Carbamimidoyl-2-(2-methoxyethoxy)phenyl]-2-(R)-{1-[4-(6-oxo-1,6-dihydropyridin-3-yl)benzoyl]pyrrolidin-2yl}propionic acid methyl ester as a crude residue which was used without further purification. A portion of this material (0.079 g, 0.16 mmol) is treated with methylene chloride (10 mL) and trifluroacetic acid (6.6 mL) at 0° C. for 2.5 h. The reaction contents are concentrated and purified by reverse phase HPLC (20-80% $CH_3CN$/0.1% TFA in water over 30 min) to give the title compound as a white solid (0.043 g, 0.07 mmol). $^1$H NMR (DMSO-$d_6$, 300 MHz) □10.68(s, 1H), 8.97(s, 2H), 8.64(s, 2H), 7.67-7.40(m, 6H), 6.88(d, 1H), 6.45(d, 1H), 4.55-4.40(m, 1H), 3.48(s, 3H), 3.32-3.15(m, 3H), 2.95-2.80(m, 2H), 2.05-1.56(m, 4H). MS m/z: $[M+H]^+$=489.

EXAMPLE 14

2-(R)-[1-(Biphenyl-4-carbonyl)-(R)-pyrrolidin-2-yl]-3-(R)-(3-carbamimidoyl-phenyl)-propionic acid methyl ester-trifluoroacetate The title compound (0.19 g, 0.33 mmol) is prepared from biphenyl-4-carboxylic acid (0.15 g, 0.77 mmol) and 3-(R)-(3-Cyanophenyl)-2-(R)-(pyrrolidin-2-yl)-propionic acid methyl ester (0.20 g, 0.77 mmol) by the methods described in EXAMPLE 12. $^1$H NMR (DMSO-$d_6$, 300 MHz) □9.25(s, 2H), 9.08(s, 2H), 7.78-7.32(m, 13H), 4.53(m, 1H), 3.52(s, 3H), 3.51-3.33(m, 3H), 3.15-2.98(s, 1H), 2.93-2.80(m, 1H), 2.04-1.60(m, 4H). MS m/z: $[M+H]^+$=456. Elemental analysis calculated with 1.5 mole of $H_2O$: C=60.40, H=5.58, N=7.04, found C=60.41, H=5.14, N=6.78.

Chiral HPLC analysis indicates the presence of one stereoisomer.

EXAMPLE 15

3-(2-{1-[4-(6-Oxo-1,6-dihydro-pyridin-3-yl)-benzoyl]-pyrrolidin-2-(R,S)-yl}-ethyl)-benzamidine-trifluoroacetate

A. 5-Methoxy-3,4-dihydro-2H-pyrrole

2-Pyrrolidone (15 g, 176.2 mmol) is added dropwise over 2 h. to a stirred solution of Dimethyl Sulfate (22.2 g, 176.2 mmol) under nitrogen and stirred at 60 C for 16 h. The reaction is cooled to RT and poured into cold saturated potassium carbonate (50 mL) and extracted with methylene chloride (3×150 mL). The organic fractions are combined, washed with brine (100 mL) and dried over $Na_2SO_4$. The organic material is concentrated at 20° C. and vacuum distilled at 35° C. to 50° C. at 16 mTorr to give the title compound as a clear oil (5.38 g, 54.3 mmol). $^1$H NMR ($CDCl_3$, 300 MHz) □03.95(s, 3H), 3.80-3.65(m, 2H), 2.60-2.50(m, 2H), 2.60-2.03(m, 2H).

B. 2,2-dimethyl-5-pyrrolidin-2-ylidene-[1,3]dioxane-4,6-dione

A solution of 5-Methoxy-3,4-dihydro-2H-pyrrole (5.35 g, 54.0 mmol), isopropylidene malonate (7.78 g, 54.0 mmol), triethylamine (1.35 mL, 9.7 mmol) and benzene (55 mL) is refluxed under nitrogen overnight. The reaction is cooled to RT and concentrated and the crude product is recrystalized from EtOH (95 mL) to give the title compound as a white solid (8.13 g, 38.5 mmol). $^1$H NMR ($CDCl_3$, 300 MHz) □3.73(t, 2H), 3.35(t, 2H), 2.20-2.08(m, 2H), 1.66(s, 6H).

C. Pyrrolidin-2-ylidene-acetic acid methyl ester

To a flask containing $NaOCH_3$ (1.21 g, 21.3 mmol) and dry MeOH (50 mL) under nitrogen is added 2,2-dimethyl-5-pyrrolidin-2-ylidene-[1,3]dioxane-4,6-dione (4.5 g, 21.3 mmol) and the contents are refluxed overnight. The reaction is concentrated and the residue is diluted with $H_2O$ (50 mL). 1 N HCl is added to obtain a pH of 6 and the mixture is extracted with $CHCl_3$ (3×30 mL). The organic fractions are combined, dried over $MgSO_4$ and concentrated. The crude product is purified by flash chromatography (50% EtOAc/hexanes) to give the title cormpouiid as a white solid (2.57 g, 18.2 mmol). $^1$H NMR ($CDCl_3$, 300 MHz) ☐4.49(br. s, 1H), 3.63(s, 3H), 3.62-3.46(m, 2H), 1.75-1.50(m, 2H), 2.11-1.90(m, 2H).

D. 3-(3-Cyano-phenyl)-2-pyrrolidin-2-ylidene-propionic acid methyl ester

To a flask containing a 60% dispersion of NaH (0.91 g, 22.7 mmol), and toluene (60 mL), under nitrogen, is added Pyrrolidin-2-ylidene-acetic acid methyl ester (3.2 g, 22.7 mmol) and the mixture is refluxed for 1 h. The reaction mixture was cooled to 0° C. and a solution of m-cyanobenzylbromide (4.45 g, 22.7 mmol) in toluene (60 mL) is added dropwise. The reaction is allowed to warm to RT and then heated at 60° C. overnight. The mixture is cooled to RT and with vigorous stirring 1 N HCl is added to obtain a pH of 6. The toluene was decanted and dried over $Na_2SO_4$ and concentrated. Purification by flash chromatography (9:9:1 of $CH_2Cl_2$:hexanes:EtOAc) gave the title compound as a wet solid (3.2 g, 12.5 mmol). $^1$H NMR ($CDCl_3$, 300 MHz) ☐8.32(br. s, 1H), 7.48-7.25(m, 4H), 3.63(s, 3H), 3.62-3.55(m, 2H), 3.53(s, 2H), 2.66-2.48(m, 2H), 2.10-1.90(m, 2H).

E. 3-[2-(4,5-Dihydro-3H-pyrrol-2-yl)-ethyl]benzonitrile

A flask containing 3-(3-Cyano-phenyl)-2-pyrrolidin-2-ylidene-propionic acid methyl ester (0.25 g, 0.977 mmol), and $H_3BO_3$ (0.0664 g, 1.07 mmol) is heated to 180° C. for 2 h. The reaction is cooled to RT and treated with $H_2O$ (0.8 mL) and $CH_2Cl_2$ (2 mL) and the resulting mixture is vigorously stirred. The organic phase is separated, diluted with $CH_2Cl_2$ (15 mL) dried over $Na_2SO_4$ and concentrated. Purification by flash chromatography (2:1:1/EtOAc:$CH_2Cl_2$:hexanes) yields the title compound (0.07 g, 0.35 mmol). $^1$H NMR ($CDCl_3$, 300 MHz) ☐7.63-7.35(m, 4H), 4.08-3.95(m, 2H), 3.18-3.01(m, 4H), 2.87-2.73(m, 2H), 2.20-2.06(m, 2H).

F. 3-(2-Pyrrolidin-2-(R,S)-ylethyl)-benzonitrile

A flask containing 3-[2-(4,5-Dihydro-3H-pyrrol-2-yl)-ethyl]benzonitrile (0.22 g, 1.11 mmol) and absolute EtOH (10 mL) was stirred under nitrogen at 0° C. To this was added $NaBH_4$ (0.063 g, 1.66 mmol) in one portion and the reaction is warmed to room temperature and stirred 1 h. The reaction is concentrated and the residue diluted with $H_2O$ (15 mL). 1 N HCl (15 mL) is added and the solution is washed with ether. The aqueous phase is basified with solid sodium carbonate and extracted with EtOAc (3×25 mL). The combined organic extracts are dried over $MgSO_4$ and concentrated to give the title compound as a yellow oil (0.10 g, 0.50 mmol). $^1$H NMR ($CDCl_3$, 300 MHz) ☐7.55-7.30(m, 4H), 4.01, 3.82(two m, 1H), 3.66-3.22(m, 2H), 3.05-2.55(m, 2H), 2.33-1.60(m, 6H).

G. 3-(2-{1-[4-(6-Methoxy-pyridin-3-yl)-benzoyl]-pyrrolidin-2-(R,S)-yl}-ethyl)-benzonitrile A flask containing 4-(6-Methoxy-pyridin-3-yl)-benzoic acid (0.114 g, 0.5 mmol) and DMF (3 mL) is stirred. To this is added Diisopropylethylamine (87 uL, 0.5 mmol) followed by TBTU (0.16 g, 0.5 mmol) and stirred 2 minutes. A solution of 3-(2-Pyrrolidin-2-(R,S)-ylethyl)-benzonitrile (0.10 g, 0.5 mmol) and DMF (1 mL) is added and the reaction stirred for 24 h. The reaction mixture is diluted with EtOAc (100 mL) and washed with saturated sodium bicarbonate (4×20 mL), brine (25 mL), dried over $MgSO_4$ and concentrated. Purification by flash chromatography (1:1/EtOAc:Hexanes) gives the title compound as a clear oil (0.09 g, 0.22 mmol). $^1$H NMR ($CDCl_3$, 300 MHz) ☐8.38(s, 1H), 7.81(d, 1H), 7.65-7.35(m, 8H), 6.83(d, 1H), 4.40-4.25 (m, 1H), 3.97(s, 3H), 3.58-3.45(m, 2H), 2.82-2.68(m, 2H), 2.45-2.30(m, 1H), 2.25-2.10(m, 1H), 2.02-1.86(m, 1H), 1.85-1.65(m, 3H).

H. 3-(2-{1-[4-(6-Oxo-1,6-dihydro-pyridin-3-yl)-benzoyl]-pyrrolidin-2-(R,S)-yl}-ethyl)-benzamidine-trifluoroacetate A flask containing 3-(2-{1-[4-(6-Methoxy-pyridin-3-yl)-benzoyl]-pyrrolidin-2-(R,S)-yl}-ethyl)-benzonitrile (0.09 g, 0.22 mmol), and pyridine hydrochloride (0.41 g, 2.62 mmol) is heated to 160° C. for 10 minutes. The molten mixture is cooled and $H_2O$ (15 mL) is added. The flask contents are partitioned between $CH_2Cl_2$ (25 mL) and saturated sodium bicarbonate (10 mL). The organic phase is separated, washed with water (10 mL), dried over $Na_2SO_4$ and concentrated to give 3-(2-{1-[4-(6-Oxo-1,6-dihydro-pyridin-3-yl)benzoyl]-pyrrolidin-2-yl}-benzonitrile which is used without further purification (0.045 g, 0.113 mmol).

A solution of 3-(2-{1-[4-(6-oxo-1,6-dihydro-pyridin-3-yl)-benzoyl]-pyrrolidin-2-yl}-ethyl)-benzonitrile (0.045 g, 0.113 mmol) in dry MeOH (10 mL) and dry $CH_2Cl_2$ (2 mL) under nitrogen was stirred at 0° C. HCl gas was bubbled through the solution for 5 minutes. The flask is sealed with a septum and stirred overnight at RT. The reaction mixture is concentrated, the residue is dissolved in dry MeOH (20 mL) and stirred under nitrogen at 0° C. Ammonia gas is bubbled through the solution for 5 minutes and the reaction stirred at 55° C. for 3 h. The reaction is concentrated and the residue is purified by reverse phase HPLC (gradient elution of 20 to 80% acetonitrile/0.1% TFA in water) and lyopholized to give the title compound as a white solid (0.011 g, 0.021 mmol). $^1$H NMR (DMSO-$d_6$, 300 MHz) ☐9.25(s, 2H), 8.85(s, 2H), 7.84(d, 1H), 7.75(s, 1H), 7.70-7.40(m, 7H), 6.42(d, 1H), 4.15(m, 1H), 3.40-3.22(m, 2H), 2.80-2.61(m, 2H), 2.30-2.15(m, 1H), 2.12-1.99(m, 1H), 1.98-1.81(m, 1H), 1.80-1.60(m, 3H). MS m/z: [M+H]$^+$=415.

EXAMPLE 16

4-Hydroxy-3-(2-{1-[4-(6-oxo-1,6-dihydro-pyridin-3-yl)-benzoyl]-pyrrolidin-2-(R)-yl}vinyl)-benzamidine trifluoroacetate

A. 2-(R)-Formyl-pyrrolidine-1-carboxylic acid tert-butyl ester

A flask containing DMSO (7.73 mL, 108.6 mmol) and $CH_2Cl_2$ (150 mL) under nitrogen is stirred at −78° C. A 2M solution of oxalyl chloride in $CH_2Cl_2$ (36.25 mL, 72.5 mmol) is added dropwise and the reaction is stirred for 10 minutes at −78° C. A solution of Boc-D-prolinol (7.05 g, 35.02 mmol) in $CH_2Cl_2$ (70 mL) was added dropwise and the reaction stirred at −78° C. for 20 minutes. Triethylamine (19.53 mL, 140 mmol) was added to the mixture and the reaction allowed to warm to RT. The reaction was poured into H₂O (40 mL) and the organic phase removed. The aqueous phase was saturated with NaCl and extracted with CH₂Cl₂ (2×75 mL). The organic fractions were combined, dried over MgSO₄ and concentrated. Purification by flash chromatography 25% EtOAc/Hexanes gave the title compound as a yellow oil (6.70 g, 33.65 mmol). ¹H NMR (CDCl₃, 300 MHz) ☐9.45(d, 1H), 4.18, 4.04(two m, 1H), 3.62-3.35(m, 2H), 2.20-1.78(m, 4H), 1.46, 1.42(two s, 9H).

B. 2-(R)-Vinyl-pyrrolidine-1-carboxylic acid tert-butyl ester

A flask containing a suspension of methyltriphenylphosphonium bromide (24.04 g, 67.3. mmol) and THF (375 mL) is stirred under nitrogen at −78° C. To this was added a 2.5 M solution of nBuLi in hexane (26.92 mL, 67.3 mmol) over 1 h. A solution of 2-(R)-Formyl-pyrrolidine-1-carboxylic acid tert-butyl ester (6.70 g, 33.65 mmol) in THF (30 mL) is added over 10 minutes and the reaction is warmed to RT. The reaction is quenched with H₂0 (180 mL) and the mixture concentrated. The residue is extracted with EtOAc (3×150 mL) and the combined extracts are dried over MgSO₄ and concentrated. Purification by flash chromatography 20% EtOAc/Hexanes yields the title compound as a yellow oil (5.2 g, 26.4 mmol). ¹H NMR (CDCl₃, 300 MHz) ☐5.81-5.63(m, 1H), 5.03(d, 2H), 4.40-4.15(m, 1H), 3.45-3.25(m, 2H), 2.05-1.90(m, 1H), 1.89-1.75(m, 2H), 1.74-1.61(m, 1H), 1.43(s, 9H).

C. 4-Hydroxy-3-(2-{1-[4-(6-oxo-1,6-dihydro-pyridin-3-yl )-benzoyl]-pyrrolidin-2-(R)-yl}vinyl)-benzamidine trifluoroacetate A flask containing 2-(R)-Vinyl-pyrrolidine-1-carboxylic acid tert-butyl ester (0.5 g, 2.54 mmol), 3-Bromo-4-(2-methoxyethoxymethoxy)-benzonitrile (1.45 g, 5.08 mmol), Bis(triphenyl-phosphine)-palladium(II) chloride (0.18 g, 0.254 mmol), triethylamine (1.77 mL, 12.7 mmol) and DMF (3 mL) is heated at 100° C. for 72 h. under nitrogen. The reaction is cooled to RT, diluted with CH₂Cl₂ (100 mL) and washed with H₂O (2×50 mL), brine (50 mL), dried over MgSO₄ and concentrated. Purification by flash chromatography (4:4:1/CH₂Cl₂:hexanes:EtOAc) provides a mixture (0.35 g) of the desired product 2-{2-[5-Cyano-2-(2-methoxy-ethoxymethoxy)-phenyl]-vinyl}-pyrrolidine-1-carboxylic acid tert-butyl ester and some of the starting alkene. This material is used directly in the next step.

A flask containing 2-(R)-{2-[5-Cyano-2-(2-methoxy-ethoxymethoxy)-phenyl]-vinyl}-pyrrolidine-1-carboxylic acid tert-butyl ester (0.110 g, 0.274 mmol) and dry MeOH (5 mL) is stirred at 0° C. HCl gas is bubbled through the solution for 5 minutes. The flask is sealed with a septum and stirred overnight at RT. The reaction is concentrated and the residue is dissolved in dry MeOH (20 mL) and stirred under nitrogen at 0° C. Ammonia gas is bubbled through the solution for 5 minutes and the reaction is stirred at 55° C. for 3 h. The reaction is concentrated and the residue is purified by reverse phase HPLC (2% acetonitrile/0.0125% aqueous HCl) and lyophilized to give the title compound (0.016 g, 0.0526 mmol).

To a stirred flask containing 4-(6-Oxa-1,6-dihydro-pyridin-3-yl-benzoic acid (0.0118 g, 0.0526 mmol) and DMF (0.5 mL) is added Diisopropylethylamine (9.15 uL, 0.0526 mmol) followed by TBTU (0.0169 g, 0.0526 mmol) the resulting solution is stirred for 2 minutes. A solution of 4-Hydroxy-3-(2-pyrrolidin-2-(R)-yl-vinyl)-benzamidine dihydrochloride (0.016 g, 0.0526 mmol) and DMF (1 mL) is added followed by Diisopropylethylamine (9.15 uL, 0.0526 mmol) and the reaction is stirred for 12 h at 35° C. The solvent is removed by Vortex blower, purified by reverse phase HPLC (gradient elution of 10% to 60% acetonitrile/ 0.1% aqueous TFA) and lyophilized to give the title compound as a white solid (0.0189 g, 0.0345 mmol). ¹H NMR (DMSO-d₆, 300 MHz) ☐9.14-8.93(m, 2H), 8.73(s, 2H), 7.98-7.68(m, 3H), 7.67-7.35(m, 5H), 7.02-6.86(m, 1H), 6.74 (d, 1H), 6.52-6.15(m, 2H), 4.81, 4.53(two m, 1H), 3.60-3.31 (m, 2H), 2.22-2.02(m, 1H), 1.99-1.67(m, 3H). MS m/z: [M+H]⁺=429.

EXAMPLE 17

4-Hydroxy-3-(2-{1-[4-(6-oxo-1,6-dihydro-pyridin-3-yl)-benzoyl]-pyrrolidin-2-(R)-yl}-ethyl)-benzamidine trifluoroacetate 4-Hydroxy-3-(2-{1-[4-(6-oxo-1,6-dihydro-pyridin-3-yl)-benzoyl]pyrrolidin-2-(R)-yl}-vinyl)benzamidine trifluoroacetate (0.0065 g, 0.01198 mmol) in MeOH (10 mL) and 5% Pd/C (catalytic amt.) is hydrogenated using a balloon filled with H₂ gas for 4 h. The reaction is filtered, evaporated and the residue is diluted with H₂O (10 mL). The aqueous solution is lyopholized to give the title compound as a white solid (0.0033 g, 0.00606 mmol). ¹H NMR (DMSO-d₆, 300 MHz) ☐8.97(s, 2H), 8.60(s, 2H), 7.93-7.26(m, 8H), 6.93(d, 1H), 6.42(d, 1H), 4.15(m, 1H), 3.61-3.35(m, 1H), 2.70-2.51 (m, 2H), 2.45-1.98(m, 4H), 1.93-1.55(m, 3H). MS m/z: [M+H]⁺=431.

EXAMPLE 18

3(R)-(3-Carbamimidoyl-phenyl)-2(R)-{1-[4-(6-oxo-1,6-dihydro-pyridin-3-yl)-benzoyl]-pyrrolidin-2-yl}-propionic acid-trifluoroacetate 3(R)-(3-Carbamimidoyl-phenyl)-2(R)-{1-[4-(6-oxo-1,6-dihydro-pyridin-3-yl)-benzoyl]-pyrrolidin-2-yl}-propionic acid-methyl ester-trifluoroacetate (0.026 g, 0.0503 mmoles), as prepared in EXAMPLE 12, is dissolved in anhydrous acetonitrile (4 mL) under nitrogen. The solution is treated with iodotrimethylsilane (0.1 g, 0.503 mmoles) and the reaction stirred at 70° C. for 12 hours. The reaction is allowed to cool to ambient temperature and water (5 mL) added. Sodium bisulfite is added with stirring until the solution turns from brown to colorless. The mixture is concentrated in vacuo and the residue purified by HPLC (gradient elution of 10% to 70% acetonitrile/0.1% aqueous TFA) and lyophilized to give the title compound as a glass (0.0163 g, 0.0285 mmoles). ¹H NMR (DMSO-d₆, 300 MHz) ☐∥☐☐br.s, 1H), 7.90-7.30(m, 10H), 6.41(d, 1H), 4.56-4.43 (m, 1H), 3.45-3.20(m, 3H), 3.15-2.95(m, 1H), 2.90-2.70(m, 1H), 2.05-1.78(m, 3H), 1.75-1.58(m, 1H). MS m/z: [M+H]⁺ =459.

The molecules described herein inhibit blood coagulation by virtue of their ability to inhibit the activity of Factor Xa. Both free Factor Xa and Factor Xa assembled in the prothrombinase complex (Factor Xa, Factor Va, calcium and phospholipid) are inhibited. Factor Xa inhibition is obtained by direct complex formation between the inhibitor and the enzyme and is therefore independent of the plasma co-factor antithrombin III. Effective Factor Xa inhibition is achieved by administering the compounds either by oral administration, continuous intravenous infusion, bolus intravenous administration or any other parenteral route such that it achieves the desired effect of preventing the Factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic. thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

The compounds of formula (I) may be used alone or in combination with other diagnostic, cardioprotective agents, direct thrombin inhibitors, anticoagulants, antiplatelet or fibrinolytic agents, selected from: anti-coagulants such as warfarin or heparin; synthetic pentasaccharides; anti-platelet agents such as aspirin, piroxicam or ticlopidine; direct thrombin inhibitors (e.g. boroarginine derivatives, hirudin or argatroban (Novastan®)); fibrinogen receptor antagonists; statins/fibrates; or fibrinolytic agents (thrombolytic agents) such as tissue plasminogen activator, anistreplase (Eminase®), urokinase or streptokinase; or combinations thereof.

The term cardioprotective agents as used herein, denotes agents that act to protect myocardium during ischemia. These cardioprotective agents include, but are nor limited to, adenosine agonists, β-blockers and Na/H exchange inhibitors. Adendosine agonists include those compounds disclosed in Spada et al., U.S. Pat. No. 5,364,862 and Spada et al., U.S. Pat. No. 5,736,554, the disclosures of which are hereby incorporated herein by reference. An example of an adenosine agonists is AMP 579 (Rhone-Poulenc Rorer). An example of a Na/H exchange inhibitor is Cariporide (HOE 642).

The term anti-coagulant agents as used herein, denotes agents that inhibit blood coagulation. Such agents include warfarin (Coumadin®) and heparin.

The term anti-platelet agents as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam (Feldane®), including pharmaceutically acceptable salts or prodrugs thereof. Other suitable anti-platelet agents include ticlopidine (Ticlid), thromboxane-A2-receptor antagonists and thromboxane-A2-synthetase inhibitors, as well as pharmaceutically acceptable salts or prodrugs thereof.

The phrase direct thrombin inhibitors (i.e. Factor IIa inhibitors), as used herein, denotes inhibitors of the serine protease thrombin. By inhibiting thrombin directly, the inhibition of the cleavage of fibrinogen to fibrin, activation of Factor XIIIa, activation of platelets, and feedback of thrombin to the coagulation cascade to generate more thrombin, occurs. Such direct inhibitors include boroarginine derivatives and boropeptides, hirudin and argatroban (Novastan®), including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The phrase fibrinolytic agents (or thrombolytics or fibrinolytics), as used herein, denotes agents that lyse blood clots. Such agents include tissue plasminogen activator, anistreplase (Eminase®), urokinase or streptokinase, including pharmaceutically acceptable salts or prodrugs thereof. Tissue plasminogen activator (tPA) is commercially available from Genentech Inc., South San Francisco, Calif. The term urokinase, as used herein, is intended to denote both dual and single chain urokinase, the latter also being referred to herein as prourokinase.

The compounds described herein may :be administered to treat-thrombotic complications in a variety of animals such as primates including humans. Inhibition of factor Xa is useful not only in the anticoagulant therapy of individuals having thrombotic conditions but is useful whenever inhibition of blood coagulation is required such as to prevent coagulation of stored whole blood and to prevent coagulation in other biological samples for testing or storage. Thus, any inhibitor of Factor Xa activity can be added to or contacted with any medium containing or suspected of containing Factor Xa and in which it is desired that blood coagulation be inhibited.

In addition to their use in anticoagulant therapy, Factor Xa inhibitors may find utility in the treatment or prevention of other diseases in which the generation of thrombin has been implicated as playing a pathologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor. Inhibition of Factor Xa will effectively block thrombin generation and therefore neutralize any pathologic effects of thrombin on various cell types.

According to a further feature of the invention there is provided a method for the treatment of a human or animal patient suffering from, or subject to, conditions which can be ameliorated by the administration of an inhibitor of Factor Xa, for example conditions as hereinbefore described, which comprises the administration to the patient of a pharmaceutically effective amount of compound of formula I or a composition containing a compound of formula I.

The present invention also includes within its scope pharmaceutical formulations which comprise at least one of the compounds of Formula I in association with a pharmaceutically acceptable carrier or coating.

In practice compounds of the present invention may generally be administered parenterally, intravenously, subcutaneously intramuscularly, nasally, colonically, nasally, intraperitoneally, rectally or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The compounds of the present invention may also be formulated for use in conjunction with other therapeutic agents such as agents or in connection with the application of therapeutic techniques to address pharmacological conditions which may be ameliorated through the application of a compound of formula I, as described herein.

The compounds of the present invention may be used in combination with any anticoagulant, antiplatelet, antithrombotic or profibrinolytic agent. Often patients are concurrently treated prior, during and after interventional procedures with agents of these classes either in order to safely perform the interventional procedure or to prevent deleterious effects of thrombus formation. Some examples of classes of agents known to be anticoagulant, antiplatelet, antithrombotic or profibrinolytic agents include any formulation of heparin, low molecular weight heparins, pentasaccharides, fibrinogen receptor antagonists, thrombin inhibitors, Factor Xa inhibitors, or Factor VIIa inhibitors.

The compounds of the present invention may be used in combination with any antihypertensive agent or cholesterol or lipid regulating agent, or concurrently in the treatment of restenosis, atherosclerosis or high blood pressure. Some examples of agents that are useful in combination with a compound according to the invention in the treatment of high blood pressure include compounds of the following classes; beta-blockers, ACE inhibitors, calcium channel antagonists and alpha-receptor antagonists. Some examples of agents that are useful in combination with a compound according to the invention in the treatment of elevated cholesterol levels or disregulated lipid levels include compounds known to be HMGCoA reductase inhibitors, compounds of the fibrate class, It is understood that the present invention includes combinations of compounds of the present invention with one or more of the aforementioned therapeutic class agents Compounds within the scope of the present invention exhibit marked pharmacological activities according to tests described in the literature and below which tests results are believed to correlate to pharmacological activity in humans and other mammals.

Enzyme Assays

The ability of the compounds in the present invention to act as inhibitors of Factor Xa, thrombin, trypsin, tissue-plasminogen activator (t-PA), urokinase-plasminogen activator (u-PA), plasmin and activated protein C is evaluated by determining the concentration of inhibitor which resulted in a 50% loss in enzyme activity (IC50) using purified enzymes.

All enzyme assays are carried out at room temperature in 96-well microtiter plates using a final enzyme concentration of 1 nM. The concentrations of Factor Xa and thrombin are determined by active site titration and the concentrations of all other enzymes are based on the protein concentration supplied by the manufacturer. Compounds according to the invention are dissolved in DMSO, diluted with their respective buffers and assayed at a maximal final DMSO concentration of 1.25%. Compound dilutions are added to wells containing buffer and enzyme and pre-equilibrated for between 5 and 30 minutes. The enzyme reactions are initiated by the addition of substrate and the color developed from the hydrolysis of the peptide-p-nitroanilide substrates is monitored continuously for 5 minutes at 405 nm on a Vmax microplate reader (Molecular Devices). Under these conditions, less than 10% of the substrate is utilized in all assays. The initial velocities measured are used to calculate the amount of inhibitor which resulted in a 50% reduction of the control velocity (IC50). The apparent Ki values are then determined according to the Cheng-Prusoff equation (IC50=Ki[1+[S]/Km]) assuming competitive inhibition kinetics.

An additional in vitro assay may be used to evaluate the potency of compounds according to the invention in normal human plasma. The activated partial thromboplastin time is a plasma-based clotting assay that relies on the in situ generation of Factor Xa, its assembly into the prothrombinase complex and the subsequent generation of thrombin and fibrin which ultimately yields the formation of a clot as the assay endpoint. This assay is currently used clinically to monitor the ex vivo effects of the commonly used anticoagulant drug heparin as well as direct acting antithrombin agents undergoing clinical evaluation. Therefore, activity in this in vitro assay is considered as a surrogate marker for in vivo anticoagulant activity.

Human Plasma Based Clotting Assay

Activated partial thromboplastin clotting times are determined in duplicate on a MLA Electra 800 instrument. A volume of 100 µl of citrated normal human pooled plasma (George King Biomedical) is added to a cuvette containing 100 µl of a compound according to the invention in Tris/NaCl buffer (pH 7.5) and placed in the instrument. Following a 3 minute warming period the instrument automatically adds 100 µl of activated cephaloplastin reagent (Actin, Dade) followed by 100 µl of 0.035 M CaCl$_2$ to initiate the clotting reaction. Clot formation is determined spectrophotometrically and measured in seconds. Compound potency is quantitated as the concentration required to double a control clotting time measured with human plasma in the absence of the compound according to the invention.

Compounds according to the invention may also be evaluated for their in vivo antithrombotic efficacy in two well established animal experimental models of acute vascular thrombosis. A rabbit model of jugular vein thrombosis a dog model of carotid artery thrombosis and a rat model of carotid artery thrombosis are used to demonstrate the antithrombotic activity of these compounds in distinct animal model paradigms of human venous thrombosis and arterial thrombosis, respectively.

Experimental in Vivo Rabbit Venous Thrombosis Model

This is a well characterized model of fibrin rich venous thrombosis that is validated in the literature and shown to be sensitive to several anticoagulant drugs including heparin (Antithrombotic Effect of Recombinant Truncated Tissue Factor Pathway Inhibitor (TFPI 1-161) in Experimental Venous Thrombosis-a Comparison with Low Molecular Weight Heparin, J. Hoist, B. Lindblad, D. Bergqvist, O. Nordfang, P. B. Ostergaard, J. G. L. Petersen, G. Nielsen and U. Hedner. Thrombosis and Haemostasis, 71, 214-219 (1994). The purpose of utilizing this model is to evaluate the ability of compounds to prevent the formation of venous thrombi (clots) in vivo generated at a site of injury and partial stasis in the jugular vein.

Male and female New Zealand white rabbits weighing 1.5-2 kg are anesthetized with 35 mg/kg of ketamine and 5 mg/kg xylazine in a volume of 1 mL/kg (i.m.). The right jugular vein is cannulated for infusion of anesthetic (ketamine/xylazine 17/2.5 mg/kg/hr at a rate of approximately 0.5 mL/hr) and administration of test substances. The right carotid artery is cannulated for recording arterial blood pressure and collecting blood samples. Body temperature is maintained at 39° C. with a GAYMAR T-PUMP. The left external jugular vein is isolated and all side branches along an exposed 2-3 cm of vessel are tied off. The internal jugular vein is cannulated, just above the bifurcation of the common jugular, and the tip of the cannula is advanced just proximal to the common jugular vein. A 1 cm segment of the vein is isolated with non-traumatic vascular clamps and a relative stenosis is formed by tying a ligature around the vein with an 18G needle just below the distal most clamp. This creates a region of reduced flow and partial stasis at the injury site. The isolated segment is gently rinsed with saline 2-3 times via the cannula in the internal jugular. Thereafter the isolated segment is filled with 0.5 mL of 0.5% polyoxyethylene ether (W-1) for 5 minutes. W-1 is a detergent which disrupts the endothelial cell lining of the segment, thus providing a thrombogenic surface for initiating clot formation. After 5 minutes the W-1 is withdrawn from the segment, and the segment is again gently rinsed with saline 2-3 times. The vascular clamps are then removed, restoring blood flow through this portion of the vessel. Clot formation is allowed to form and grow for 30 minutes after which the vein is cut just below the stenotic ligature and inspected for blood flow (the absence of blood flow is recorded as complete occlusion). The entire isolated segment of vein is then ligated and the formed clot is removed and weighed (wet weight). The effect of test agents on final clot weights is used as the primary end point. Animals are maintained for an additional thirty minutes to obtain a final pharmacodynamic measure of anticoagulation. Drug administration is initiated 15 minutes prior to vascular injury with W-1 and continued through the period of clot formation and maturation. Three blood samples (3 mL each) are obtained for evaluation of hemostatic parameters: one just prior to administration of W-1; a second 30 minutes after removal of the vascular clamps and a third at the termination of the experiment. Antithrombotic efficacy is expressed as a reduction in the final clot weight in preparations treated with a compound according to the invention relative to vehicle treated control animals.

Experimental in Vivo Rat Arterial Thrombosis Model

The antithrombotic efficacy of Factor Xa inhibitors against platelet-rich arterial thrombosis may be evaluated using a well characterized rat carotid artery $FeCl_2$-induced thrombosis model (Superior Activity of a Thromboxane Receptor Antagonist as Compared with Aspirin in Rat Models of Arterial and Venous Thrombosis, W. A. Schumacher, C. L. Heran, T. E. Steinbacher, S. Youssef and M. L. Ogletree. Journal of Cardiovascular Pharmacology, 22, 526-533 (1993); Rat Model of Arterial Thrombosis Induced by Ferric Chloride, K. D. Kurtz, B. W. Main, and G. E. Sandusky. Thrombosis Research, 60, 269-280 (1990); The Effect of Thrombin Inhibition in a Rat Arterial Thrombosis Model, R. J. Broersma, L. W. Kutcher and E. F. Heminger. Thrombosis Research 64, 405-412 (1991). This model is widely used to evaluate the antithrombotic potential of a variety of agents including heparin and the direct acting thrombin inhibitors.

Sprague Dawley rats weighing 375-450 g are anesthetized with sodium pentobarbital (50 mg/kg i.p.). Upon reaching an acceptable level of anesthesia, the ventral surface of the neck is shaved and prepared for aseptic surgery. Electrocardiogram electrodes are connected and lead II is monitored throughout the experiment. The right femoral vein and artery are cannulated with PE-50 tubing for administration of a compound according to the invention and for obtaining blood samples and monitoring blood pressure, respectively. A midline incision is made in the ventral surface of the neck. The trachea is exposed and intubated with PE-240 tubing to ensure airway patency. The right carotid artery is isolated and two 4-0 silk sutures are placed around the vessel to facilitate instrumentation. An electromagnetic flow probe (0.95-1.0 mm lumen) is placed around the vessel to measure blood flow. Distal to the probe a 4×4 mm strip of parafilm is placed under the vessel to isolate it from the surrounding muscle bed. After baseline flow measurements are made, a 2×5 mm strip of filter paper previously saturated in 35% $FeCl_2$ is placed on top of the vessel downstream from the probe for ten minutes and then removed. The $FeCl_2$ is thought to diffuse into the underlying segment of artery and cause deendothelialization resulting in acute thrombus formation. Following application of the $FeCl_2$-soaked filter paper, blood pressure, carotid artery blood flow and heart rate are monitored for an observation period of 60 minutes. Following occlusion of the vessel (defined as the attainment of zero blood flow), or 60 minutes after filter paper application if patency is maintained, the artery is ligated proximal and distal to the area of injury and the vessel is excised. The thrombus is removed and weighed immediately and recorded as the primary end point of the study.

Following surgical instrumentation a control blood sample (B1) is drawn. All blood samples are collected from the arterial catheter and mixed with sodium citrate to prevent clotting. After each blood sample, the catheter is flushed with 0.5 mL of 0.9% saline. A compound according to the invention is administered intravenously (i.v.) starting 5 minutes prior to $FeCl_2$ application. The time between $FeCl_2$ application and the time at which carotid blood flow reached zero is recorded as time to occlusion (TTO). For vessels that did not occlude within 60 minutes, TTO is assigned a value of 60 minutes. Five minutes after application of $FeCl_2$, a second blood sample is drawn (B2). After 10 minutes of $FeCl_2$ exposure, the filter paper is removed from the vessel and the animal is monitored for the remainder of the experiment. Upon reaching zero blood flow blood a third blood sample is drawn (B3) and the clot is removed and weighed. Template bleeding time measurements are performed on the forelimb toe pads at the same time that blood samples are obtained. Coagulation profiles consisting of activated partial thromboplastin time (APTT) and prothrombin time (PT) are performed on all blood samples. In some instances a compound according to the invention may be administered orally. Rats are restrained manually using standard techniques and compounds are administered by intragastric gavage using a 18 gauge curved dosing needle (volume of 5 mL/kg). Fifteen minutes after intragastric dosing, the animal is anesthetized and instrumented as described previously. Experiments are then performed according to the protocol described above.

The present invention may be embodied in other specific forms without departing from the spirit or essential attributes thereof.

What is claimed is:

1. A compound of Formula (I)

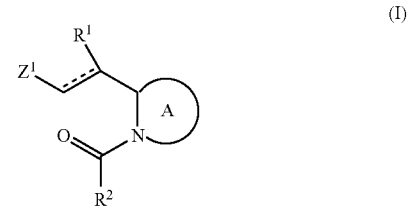

wherein

----- is a single or double bond $R^1$ is hydrogen, $-CO_2R^3$, $-C(O)R^3$, $-CONR^3R^3$, $-CH_2OR^4$ or $-CH_2SR^4$;

ring A is an optionally substituted pyrrolidinyl ring;

$R^2$ is alkyl, alkenyl, alkynyl, optionally substituted cycloalkyl, optionally substituted cycloalkenyl, optionally substituted heterocyclyl, optionally substituted heterocyclenyl, optionally substituted aryl, optionally substituted heteroaryl, optionally substituted aralkyl, optionally substituted heteroaralkyl, optionally substituted aralkenyl, optionally substituted heteroaralkenyl, optionally substituted aralkynyl, or optionally substituted heteroaralkynyl;

$R^3$ is hydrogen or lower alkyl;

$R^4$ is hydrogen, lower alkyl, lower acyl, aroyl or heteroaroyl; and $Z^1$ is optionally substituted phenyl and is additionally substituted by an amidino group of formula

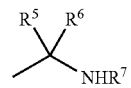

wherein $R^5$ and $R^6$ together are $=NR^8$; $R^8$ is selected from hydrogen, $R^9O_2C-$, $R^9O-$, $HO-$, $R^9C(O)-$, $HCO-$, cyano, optionally substituted lower alkyl, nitro or $Y^{1a}Y^{2a}N-$; wherein $R^9$ is alkyl, optionally substituted aralkyl, or optionally substituted heteroaralkyl; $R^7$ is selected from hydrogen, optionally substituted lower alkyl, optionally substituted aralkyl and optionally substituted heteroaralkyl; and $Y^{1a}$ and $Y^{2a}$ are independently hydrogen or alkyl; or 2. The compound according to claim 1 wherein $R^8$ is hydrogen; and $R^7$ is hydrogen; or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

3. The compound according to claim 1 wherein $R^7$ and $R^8$ are independently optionally substituted lower alkyl; or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

4. The compound according to claim 1 wherein
$R^1$ is hydrogen, —CO$_2$R$^3$, —CH$_2$OR$^4$ or —CH$_2$SR$^4$; or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

5. The compound according to claim 1 wherein
$R^1$ is hydrogen, —CO$_2$R$^3$ or —CH$_2$OR$^4$; or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarvisulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hyclroxy-1-methylpyrazolyl or other heterocyclic phenols.

6. The compound according to claim 1 wherein
$R^1$ is —CO$_2$R$^3$ and $R^3$ is lower alkyl or hydrogen; or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

7. The compound according to claim 1 wherein
$R^1$ is —CH$_2$OR$^4$ or —CH$_2$SR$^4$ and $R^4$ is hydrogen or lower alkyl; or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

8. The compound according to claim 1 wherein
$R^2$ is optionally substituted cycloalkyl, optionally substituted heterocyclyl, optionally substituted aryl, optionally substituted heteroaryl, optionally substituted aralkyl or optionally substituted aralkynyl; or a pharmaceutically acceptable salt thereof, an N-oxide thereof, or an acid bioisotere thereof selected from the group consisting of C(=O)—NHOH, C(=O)—NH—CN, sulpho, phosphono, ailcylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

9. The compound according to claim 1 wherein
$R^2$ is optionally substituted phenyl, optionally substituted naphthyl, or optionally substituted heteroaryl; or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

10. The compound according to claim 1 wherein
$R^2$ is optionally substituted (phenyl substituted phenyl), optionally substituted (heteroaryl substituted phenyl), optionally substituted (phenyl substituted heteroaryl), optionally substituted (heteroaryl substituted heteroaryl), optionally substituted (phenyl substituted heterocyclenyl), optionally substituted (phenyl substituted heterocyclyl), optionally substituted (heteroaryl substituted heterocyclenyl) or optionally substituted (heteroaryl substituted heterocyclyl); or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

11. The compound according to claim 1 wherein
$R^2$ is optionally substituted (phenyl substituted phenyl), optionally substituted (heteroaryl substituted phenyl), optionally substituted (phenyl substituted heteroaryl) or optionally substituted (heteroaryl substituted heteroaryl); or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

12. The compound according to claim 1 wherein
$R^3$ is lower alkyl; or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

13. The compound according to claim 1 wherein
$R^4$ is hydrogen or lower alkyl; or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

14. The compound according to claim 3 wherein
$R^9$ is lower alkyl; or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

15. The compound according to claim 1 wherein ----- is a single bond; or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

16. The compound according to claim 1 wherein ----- is a single bond;
$R^1$ is —CO$_2$R$^3$;
$R^2$ is optionally substituted (phenyl substituted phenyl), optionally substituted (heteroaryl substituted phenyl), optionally substituted (phenyl substituted heteroaryl), optionally substituted (heteroaryl substituted heteroaryl), optionally substituted (phenyl substituted heterocyclenyl), optionally substituted (phenyl substituted heterocyclyl), optionally substituted (heteroaryl substituted heterocyclenyl) or optionally substituted (heteroaryl substituted heterocyclyl); and
$Z^1$ is phenyl, which is substituted by an amidino substituent; or
a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

17. The compound according to claim 1 wherein $Z^1$ is substituted by an amidino group in the meta or para position of the ring system of $Z^1$, relative to the position of attachment of $Z^1$ to the rest of the molecule; or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

18. The compound according to claim 1 wherein
$R^5$ and $R^6$ together are =NR$^8$;
$R^8$ is hydrogen;
$R^7$ is hydrogen;
$R^1$ is hydrogen, —CO$_2$R$^3$, —C(O)R$^3$, —CH$_2$OR$^4$ or —CH$_2$SR$^4$;
Ring A is an optionally substituted pyrrolidinyl ring;
$R^2$ is optionally substituted cycloalkyl, optionally substituted cycloalkenyl, or optionally substituted heteroaryl;
$R^4$ is hydrogen or lower alkyl; and
----- is a single or double bond; or
a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

19. A compound according to claim 1 which is:
2-[1-(Biphenyl-4-carbonyl)-pyrrolidin-2-yl]-3-(3-carbamimidoylphenyl)-propionic acid methyl ester trifluoroacetate, 3-(3-Carbamimidoylphenyl)-2-[1-(4-pyridin-3-ylbenzoyl)-pyrrolidin-2-yl]propionic acid methyl ester ditrifluoroacetate, 2-[1-(3-Aminomethyl-biphenyl-4-carbonyl)-pyrrolidin-2-yl]-3-(3-carbamimidoylphenyl)-propionic acid methyl ester ditrifluoroacetate, 3-(3-Carbamimidoylphenyl)-2-[1-(6-chlorobenzo[b]thiophene-2-carbonyl)-pyrrolidin-2-yl]-propionic acid methyl ester trifluoroacetate, 3-(3-Carbamimidoylphenyl)-2-{1-[4-(6-methoxypyrid-3-yl)-benzoyl]-pyrrolidin-2-yl}-propionic acid methyl ester ditrifluoroacetate, 3-(3-Carbamimidoylphenyl)-2-{1-[4-(6-oxo-1,6-dihydropyrid-3-yl)-benzoyl]-pyrrolidin-2-yl}-propionic acid methyl ester trifluoroacetate, 2-[1-(Biphenyl-4-carbonyl)-pyrrolidin-2-yl]-3-(4-carbamimidoylphenyl)-propionic acid methyl ester trifluoroacetate, 3-(R)-(5-Carbamimidoyl-2-hydroxyphenyl)-2-(R)-{1-[4-(6-oxo-1,6-dihydropyrid-3-yl)-benzoyl]-pyrrolidin-2-yl}-propionic acid methyl ester trifluoroacetate, 4-Hydroxy-3-(2-{1-[4-(6-oxo-1,6-dihydro-pyridin-3-yl)-beazoyl]-pyrrolidin-2-(R)-yl}-ethyl)-benzamidine trifluoroacetate, 3(R)-(3-Carbamimidoyl-phenyl)-2(R)-{1-[4-(6-oxo-1,6-dihydro-pyridin-3-yl)-benzoyl]-pyrrolidin-2-yl}-propionic acid -trifluoroacetate; 2-(R)-[1-(Biphenyl-4-carbonyl)-(R)-pyrrolidin-2-yl]-3-(R)-(3-carbamimidoyl-phenyl)-propionic acid methyl ester-trifluoroacetate, 3-(2-{1-[4-(6-Oxo-1,6-dihydro-pyridin-3-yl)-benzoyl]-pyrrolidin-2-(R,S)-yl}-ethyl)-benzamidine-trifluoroacetate, or 4-Hydroxy-3-(2-{1-[4-(6-oxo-1,6-dihydro-pyridin-3-yl) -benzoyl]-pyrrolidin-2-(R)-yl}vinyl)-benzaniidine trifluoroacetate or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols.

20. A pharmaceutical composition comprising a pharmaceutically effective amount of the compound according to claim 1, or a pharmaceutically acceptable salt thereof, an N-oxide thereof, or an acid bioisotere thereof selected from the group consisting of C(=O)—NHOH, C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, or 3-hydroxyisoxazolyl, 3-hydroxy-1-methylpyrazolyl or other heterocyclic phenols, and a pharmaceutically acceptable carrier.

* * * * *